(12) United States Patent
Nakasuji et al.

(10) Patent No.: US 9,390,886 B2
(45) Date of Patent: Jul. 12, 2016

(54) ELECTRO-OPTICAL INSPECTION APPARATUS USING ELECTRON BEAM

(75) Inventors: Mamoru Nakasuji, Tokyo (JP); Nobuharu Noji, Tokyo (JP); Tohru Satake, Tokyo (JP); Hirosi Sobukawa, Tokyo (JP)

(73) Assignee: EBARA CORPORATION, Tokyo (JP)

( * ) Notice: Subject to any disclaimer, the term of this patent is extended or adjusted under 35 U.S.C. 154(b) by 1095 days.

(21) Appl. No.: 11/884,367

(22) PCT Filed: Feb. 17, 2006

(86) PCT No.: PCT/JP2006/002845
§ 371 (c)(1),
(2), (4) Date: Mar. 8, 2010

(87) PCT Pub. No.: WO2006/088141
PCT Pub. Date: Aug. 24, 2006

(65) Prior Publication Data
US 2010/0213370 A1  Aug. 26, 2010

(30) Foreign Application Priority Data

Feb. 17, 2005 (JP) .................. 2005-041063
Mar. 17, 2005 (JP) .................. 2005-077136

(51) Int. Cl.
*G01N 23/00* (2006.01)
*H01J 37/244* (2006.01)
(Continued)

(52) U.S. Cl.
CPC ............ *H01J 37/244* (2013.01); *G01N 23/225* (2013.01); *H01J 37/226* (2013.01); *G02F 2001/136254* (2013.01); *H01J 2237/15* (2013.01); *H01J 2237/2482* (2013.01);
(Continued)

(58) Field of Classification Search
CPC ........................... H01J 37/244; G01T 1/1645
USPC ......................................... 250/306, 310, 311
See application file for complete search history.

(56) References Cited

U.S. PATENT DOCUMENTS 3,746,855 A * 7/1973 Hilditch ........................ 250/310
4,871,912 A * 10/1989 Kokubo et al. ............... 250/311
(Continued)

FOREIGN PATENT DOCUMENTS

| JP | 10-106467 | 4/1998 |
| JP | 11-108864 | 4/1999 |

(Continued)

*Primary Examiner* — Nicole Ippolito
*Assistant Examiner* — Jason McCormack
(74) *Attorney, Agent, or Firm* — Wenderoth, Lind & Ponack, L.L.P.

(57) ABSTRACT

An electron beam apparatus for capturing images by deflecting a primary electron beam by a deflector to irradiate each of sub-visual fields which are formed by dividing an evaluation area on a sample surface, and detecting secondary electrons containing information on the sample surface in each of the sub-visual fields by a detecting device. The detecting device includes a plurality of unit detectors each including an area sensor, a bundle of optical fibers having one end coupled to a detection plane of the area sensor, and an FOP coated on the other end of the bundle of optical fibers and formed with a scintillator, on which a secondary electron beam emitted from the respective sub-visual field is focused. An electromagnetic deflector deflects the secondary electron beam each time the electron beam is irradiated to the next sub-visual field to move the secondary electron beams over the surfaces of the FOPs.

11 Claims, 17 Drawing Sheets

(51) Int. Cl.
   *G01N 23/225* (2006.01)
   *H01J 37/22* (2006.01)
   *G02F 1/1362* (2006.01)
   *H01L 27/146* (2006.01)

(52) U.S. Cl.
   CPC ....... *H01J2237/2817* (2013.01); *H01L 27/146* (2013.01); *H01L 27/14601* (2013.01)

(56) References Cited

U.S. PATENT DOCUMENTS

| | | | |
|---|---|---|---|
| 4,933,961 A * | 6/1990 | Rushbrooke et al. | 378/57 |
| 5,748,264 A * | 5/1998 | Hegg | 348/746 |
| 5,986,264 A * | 11/1999 | Grunewald | 250/310 |
| 6,051,834 A * | 4/2000 | Kakibayashi et al. | 250/311 |
| 6,130,429 A * | 10/2000 | Ambe et al. | 250/310 |
| 6,465,783 B1 * | 10/2002 | Nakasuji | 250/311 |
| 6,479,819 B1 * | 11/2002 | Hamashima et al. | 250/310 |
| 6,593,152 B2 | 7/2003 | Nakasuji et al. | |
| 7,235,799 B2 * | 6/2007 | Nakasuji et al. | 250/492.23 |
| 7,292,327 B2 * | 11/2007 | Nara et al. | 356/237.2 |
| 7,928,403 B2 * | 4/2011 | Adamec | 250/396 R |
| 2001/0050343 A1 * | 12/2001 | Kobaru et al. | 250/492.3 |
| 2002/0034411 A1 * | 3/2002 | Rusk | 401/6 |
| 2002/0084411 A1 * | 7/2002 | Yamazaki et al. | 250/306 |
| 2002/0088940 A1 * | 7/2002 | Watanabe et al. | 250/310 |
| 2002/0109090 A1 | 8/2002 | Nakasuji et al. | |
| 2002/0117635 A1 | 8/2002 | Shinada et al. | |
| 2002/0130262 A1 * | 9/2002 | Nakasuji et al. | 250/311 |
| 2002/0142496 A1 | 10/2002 | Nakasuji et al. | |
| 2003/0047682 A1 * | 3/2003 | Hatakeyama et al. | 250/310 |
| 2003/0116717 A1 * | 6/2003 | Knippelmeyer | 250/397 |
| 2003/0155509 A1 * | 8/2003 | Nakasuji et al. | 250/310 |
| 2004/0021074 A1 * | 2/2004 | Suzuki et al. | 250/306 |
| 2004/0113073 A1 * | 6/2004 | Nakasuji et al. | 250/306 |
| 2004/0159787 A1 * | 8/2004 | Nakasuji et al. | 250/311 |
| 2004/0188630 A1 * | 9/2004 | Brunner et al. | 250/396 R |
| 2004/0232321 A1 * | 11/2004 | Miles et al. | 250/235 |
| 2004/0238740 A1 * | 12/2004 | Kohama | H01J 37/28 250/310 |
| 2005/0104017 A1 | 5/2005 | Kimba et al. | |
| 2006/0060790 A1 * | 3/2006 | Nakasuji et al. | 250/423 F |

FOREIGN PATENT DOCUMENTS

| | | |
|---|---|---|
| JP | 2003-331763 | 11/2003 |
| JP | 2004-172428 | 6/2004 |
| JP | 2005-17270 | 1/2005 |
| WO | 02/37526 | 5/2002 |
| WO | 02/49065 | 6/2002 |

\* cited by examiner

Fig. 13
(A) 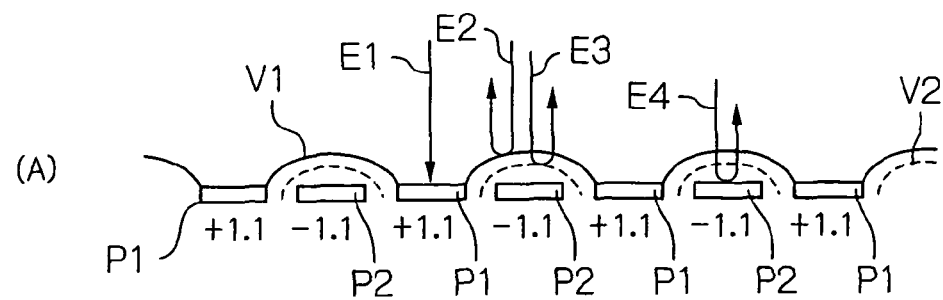
(B) 
(C) 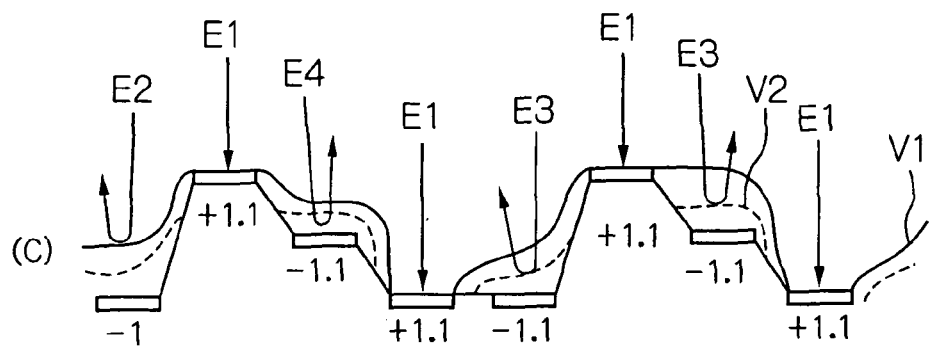
(D) 

Fig.19
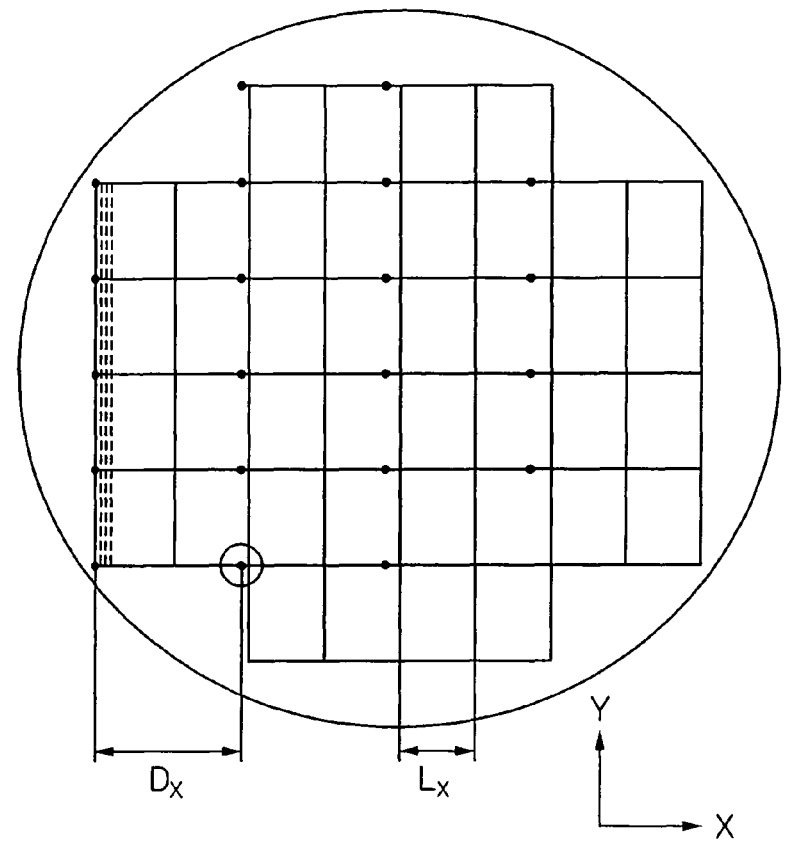
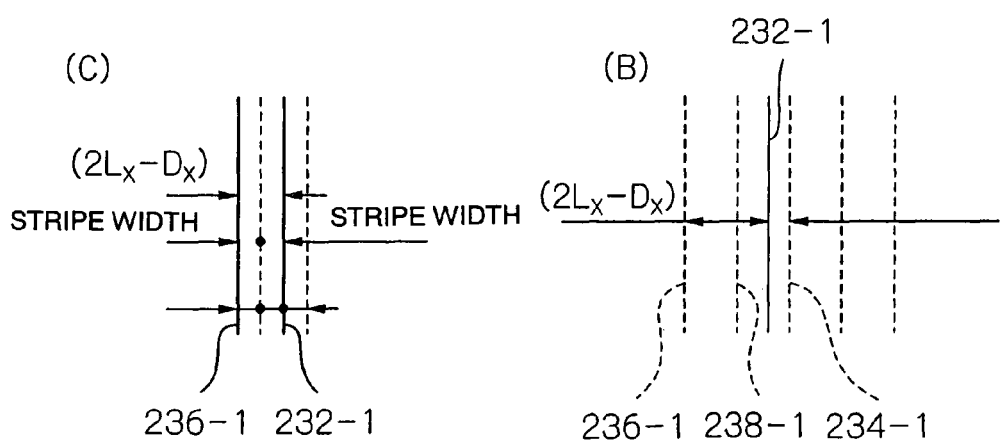

Fig.20
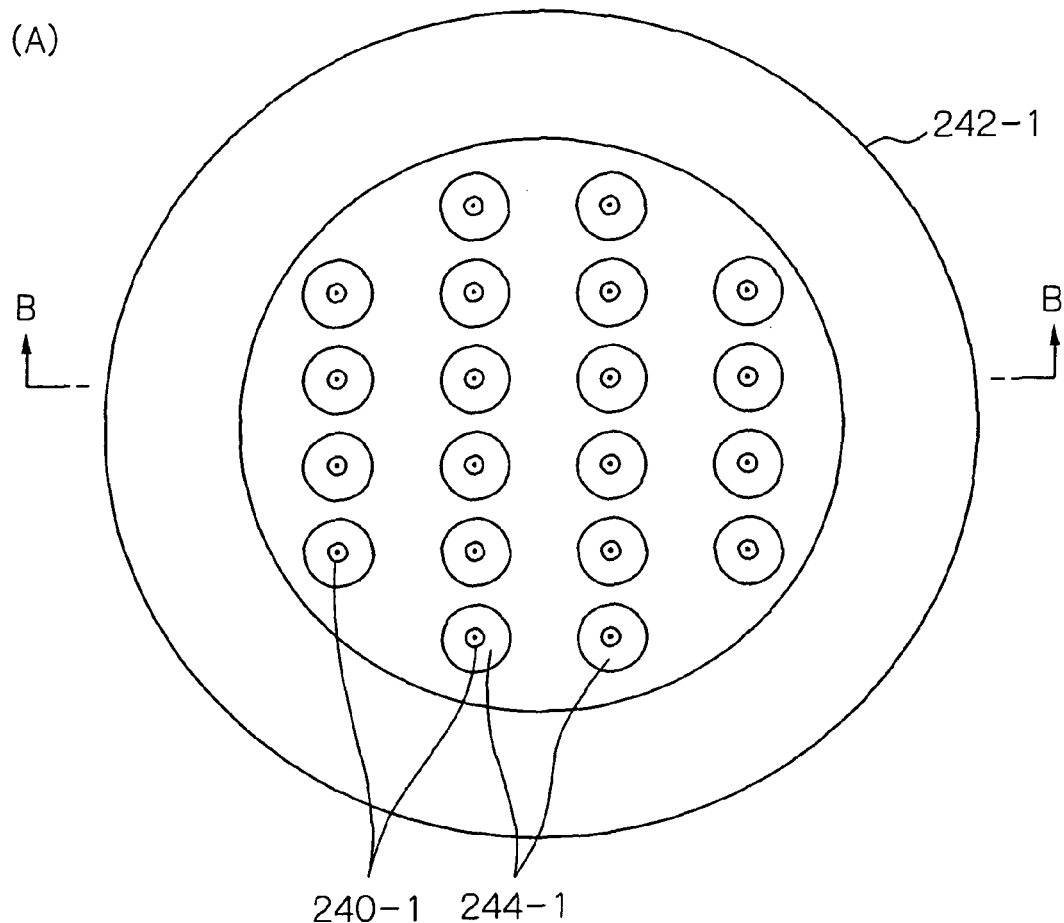
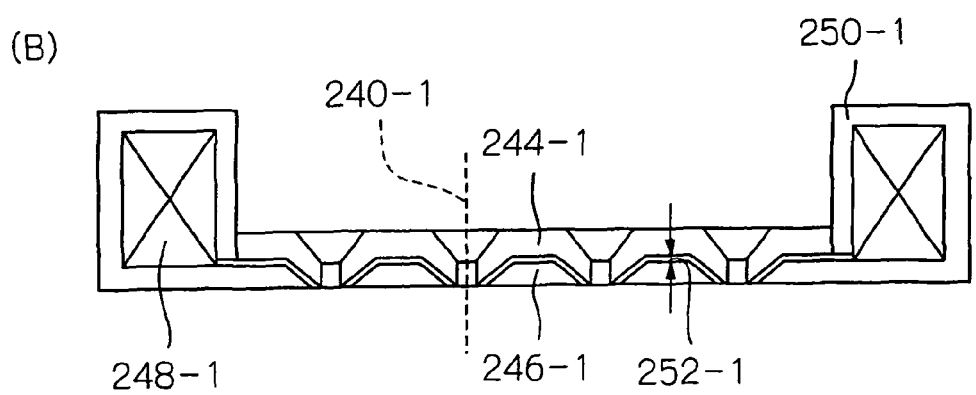

ELECTRO-OPTICAL INSPECTION APPARATUS USING ELECTRON BEAM

TECHNICAL FIELD

The present invention relates to a defect inspection apparatus for inspecting a sample formed with a pattern on the surface thereof to detect defects, and more particularly, to a defect inspection apparatus which irradiates a sample, such as a wafer with an electron beam in a semiconductor manufacturing process, captures secondary electrons and the like, which vary depending on the nature of the surface of the sample, to form image data, and evaluates defects on the pattern and the like on the sample surface on the basis of the image data at a high throughput.

BACKGROUND ART

In semiconductor manufacturing processes, design rules is about to enter a 100-nm era, and the manufacturing form is shifting from mass manufacturing of one type of product, as represented by DRAM (dynamic random access memory), to multiple types and small amount manufacturing such as SOC (silicon on chip) manufacturing. This shift is accompanied by an increased number of manufacturing steps, at each of which the yield rate must be essentially improved, with importance placed on inspections for defects caused by processes.

With higher integration of semiconductor devices and increasing miniaturization of patterns, inspection apparatuses are required to provide higher resolutions and higher throughput. In order to inspect a wafer for a 100-nm design rule to detect defects, a resolution of 100 nm or less is required. Since the amount of inspections increases due to an increased number of manufacturing steps resulting from higher integration of devices, a higher throughput is required. Also, as devices are formed of a larger number of layers, inspection apparatuses are required to provide a function of detecting defective contacts (electric defects) of via-holes which connect between wire patterns on layers.

Under the circumstances, a TDI detector having a detection rate of about 800M pixels/sec has been commercially available as an optical or electron beam detector. Further, an apparatus using a line sensor for capturing image data representative of a one-dimensional line image and an image projection type electron apparatus using an area sensor such as a CCD or CMOS image sensor for capturing image data representative of a two-dimensional image, have been provided.

An apparatus for detecting defects on a liquid crystal substrate has been provided in which a plurality of electro-optical barrels are positioned over the liquid crystal substrate. (See "NIKKEI MICRODEVICES" P. 28-P. 30, December, 2002.)

SUMMARY OF THE INVENTION

In an image projection type electron apparatus of a prior art as above, a CCD detector in which pixels can be exposed at a rate of 640×480 pixels per 100 μs, is provided. However, as to the number of CCD frames which is detectable within one second in the CCD detector, the detection rate is a several frames per second, which is longer than the minimum exposure time period of 100 μs.

Further, in a defect detection apparatus for a liquid crystal substrate of a prior art as above, since it is designed without consideration that the liquid crystal substrate contains a periodic pattern(s) thereon, and thus there is not any specific problem caused by fixing a pitch or interval of optical axes of a plurality of electro-optical barrels, the optical axes are fixed.

However, when the defect detection apparatus for a liquid crystal substrate is applied to test a sample on which a periodic pattern(s) is configured, the following problems occur.

If device products on wafers are different from each other, arrangement pitches of dies on the wafers are different from each other, in general. In defect detections for wafers having different periodic patters, since the pitch of the optical axes of the electro-optical barrels is fixed, the pitches of a pattern on a wafer and optical axes of the barrel may not match to each other. Under the condition, some of the optical axes cannot be used for the test, and even optical axes which are usable for the test, have pause time periods.

The present invention has been accomplished in view of the problems stated above. A first object of the invention is to provide an image projection type electron beam apparatus, which is capable of capturing an image at a GHz order even if an area sensor having a small number of frames per second.

A second object of the present invention is to provide an electron beam apparatus having a plurality of electro-optical barrels, which is capable of reducing problems caused by different pitches of a periodic pattern on a sample to be tested and the electro-optical barrels.

The present invention provides an electron beam apparatus to achieve the first object, in which a primary electron beam is deflected by a deflector to irradiate each of a plurality of sub-visual fields which are obtained by dividing an evaluation area on a surface of a sample, and secondary electrons containing information on the surface of the sample in each of the sub-visual fields are detected by detection means to acquire information on the evaluation area, wherein the detection means comprises a plurality of unit detectors each including an area sensor; a bundle of optical fibers having one end coupled to a detection plane of the area sensor; and, an FOP coated on the other end of the bundle of the optical fibers and formed with a scintillator, on which secondary electron beams of the sub-visual fields are focused, and the electron beam apparatus comprises an electromagnetic deflector for deflecting secondary electron beams emitted from the sub-visual fields each time the primary electron beam is irradiated to a next sub-visual field, to move the secondary electron beam over the surfaces of the FOPs of the plurality of unit detectors which form the detecting means.

It is preferable that the electron beam apparatus further comprises an electromagnetic lens including an axially symmetric electrode(s) therein, and is adapted to correct the amount of rotation of the electron beam by adjusting a voltage applied to the axially symmetric electrode. In this case, the electromagnetic lens preferably comprises two electromagnetic lenses each including an axially symmetric electrode therein, the two electromagnetic lenses rotate the electron beam in directions opposite to each other, and the two electromagnetic lenses are adapted to be independently controlled for focal distances and the amounts of rotation of the electron beam.

In the electron beam apparatus, it is preferable that the number of the unit detectors is set to a value approximated to $t_1/(t_2+t_3)$, where $t_1$ represents a time period required to fetch a signal from one area sensor, $t_2$ an exposure time period; and $t_3$ a settling time period of the electrostatic deflector. Further, it is preferable that multiple primary electron beams are employed and that a primary electro-optical system of the apparatus includes a plurality of optical axes which are formed by a plurality of lenses comprising magnetic poles or electrodes having lens gaps.

In the electron beam apparatus, when the sample contains patterns having different potentials, the information on the evaluation area is information on the potential.

In order to achieve the second object, the present invention provides an electron beam apparatus for testing a substrate using an electro-optical system having a plurality of optical axes, wherein a rotatable stage on which the substrate is carried, is rotated by an angle on the basis of information on a die pitch to test the substrate.

In this electron beam apparatus, it is preferable that when the optical axes are two-dimensionally arranged at a pitch D, and dies are arranged on the substrate at a pitch Lx in the X-axis direction and at a pitch Ly in the Y-axis direction, θ representing an angle between a line connecting the plurality of optical axes and the X-axis is determined to satisfy a relationship n*Lx−D sin θ=m*(stripe width) to test the substrate, where n, m are integers. Is this event, it is preferable that the substrate is tested by setting the integer m in a range of one to three and that when the die pitch is different from the pitch of the optical axes in the X-axis direction, the substrate is tested after rotating the stage to result in the angle θ which satisfies the relationship.

In order to achieve the second object of the invention, the present invention provides an electron beam apparatus for testing a substrate for defects using an electro-optical system having a plurality of optical axes which are arranged at an optical axis pitch Dx in the X-axis direction, wherein the substrate is tested by providing the first chip served by a second optical axis, with a stripe narrower than a standard stripe width when dies are arranged on the substrate at a die pitch Lx in the X-axis direction.

In order to achieve the second object, the invention further provides an electron beam apparatus for testing a substrate for defects using an electro-optical system having a plurality of optical axes which are arranged at an optical axis pitch Dx in the X-axis direction, wherein the substrate is tested after adjusting a stripe width such that a distance between a boundary of the dies and the optical axis, divided by a stripe width results in an integer, when dies are arranged on the substrate at a die pitch Lx in the X-axis direction.

This electron beam apparatus preferably comprises a Schottky cathode electron gun and an objective lens comprising an electrostatic lens. It is preferable that the objective lens comprises a plurality of substrates having a plurality of holes defining the optical axes, the substrates being combined in the axial direction.

BRIEF DESCRIPTION OF THE DRAWINGS

FIGS. 13(A)-13(D) are diagrams for explaining problems regarding a potential distribution detection executed by an electron beam apparatus according to a prior art;

FIGS. 19(A)-19(C) are diagrams for explaining how to set pitches of multiple optical axes and dies in an electron beam apparatus having the multiple axes according to the present invention; and FIGS. 20(A)-20(B) shows top and cross-sectional drawings of an objective lens having multiple optical axes according to the invention.

PREFERRED EMBODIMENTS OF THE INVENTION

Before describing preferred embodiments of a defect inspection apparatus or electron beam apparatus according to the present invention, description will be made of the general configuration of a semiconductor wafer inspection system which can incorporate and utilize the defect inspection apparatus according to the present invention.

Figure 1:
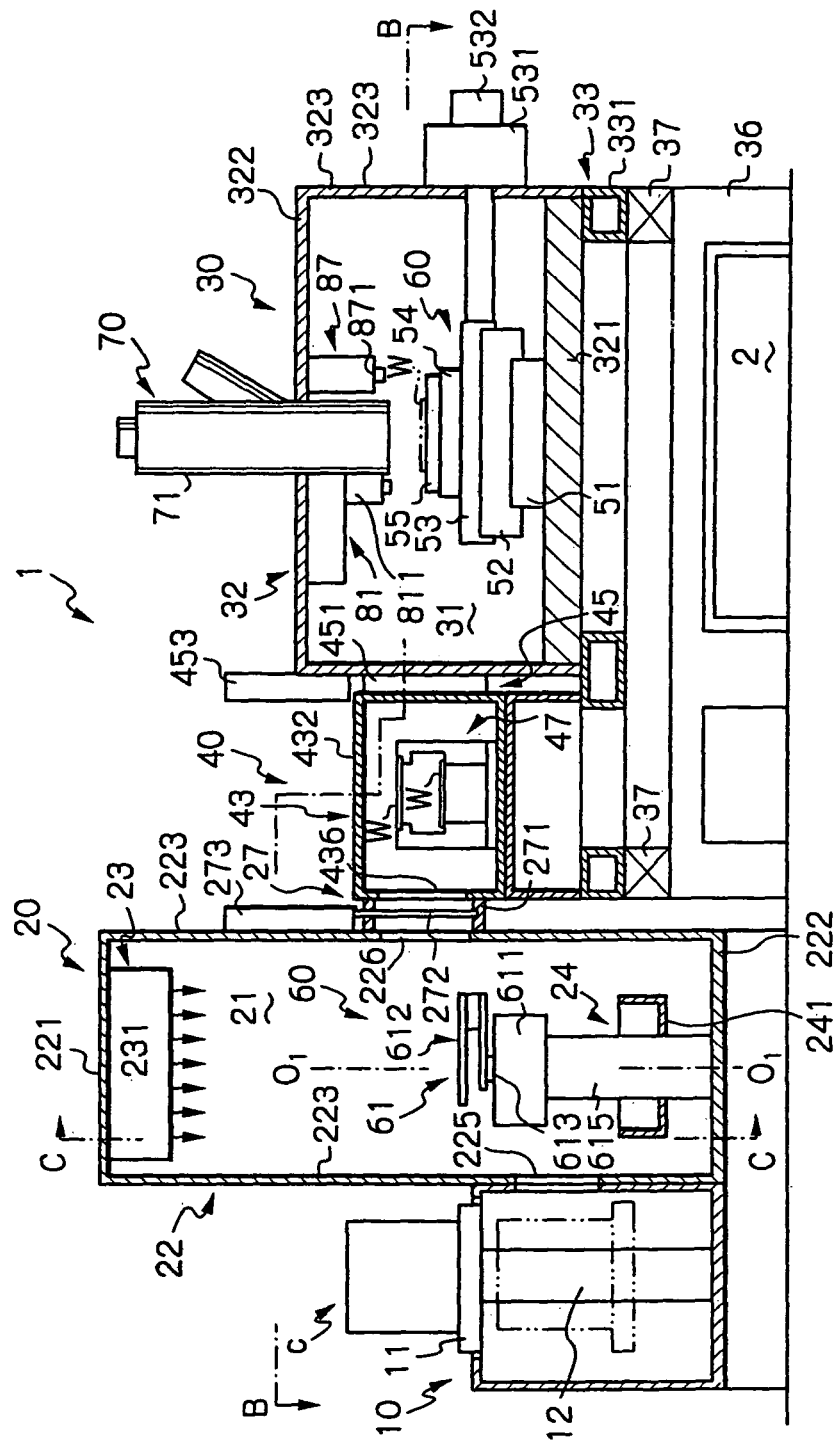
FIG. 1 is an elevation illustrating main components of a semiconductor wafer inspection system to which the defect inspection apparatus according to the present invention can be applied.
Figure 2:
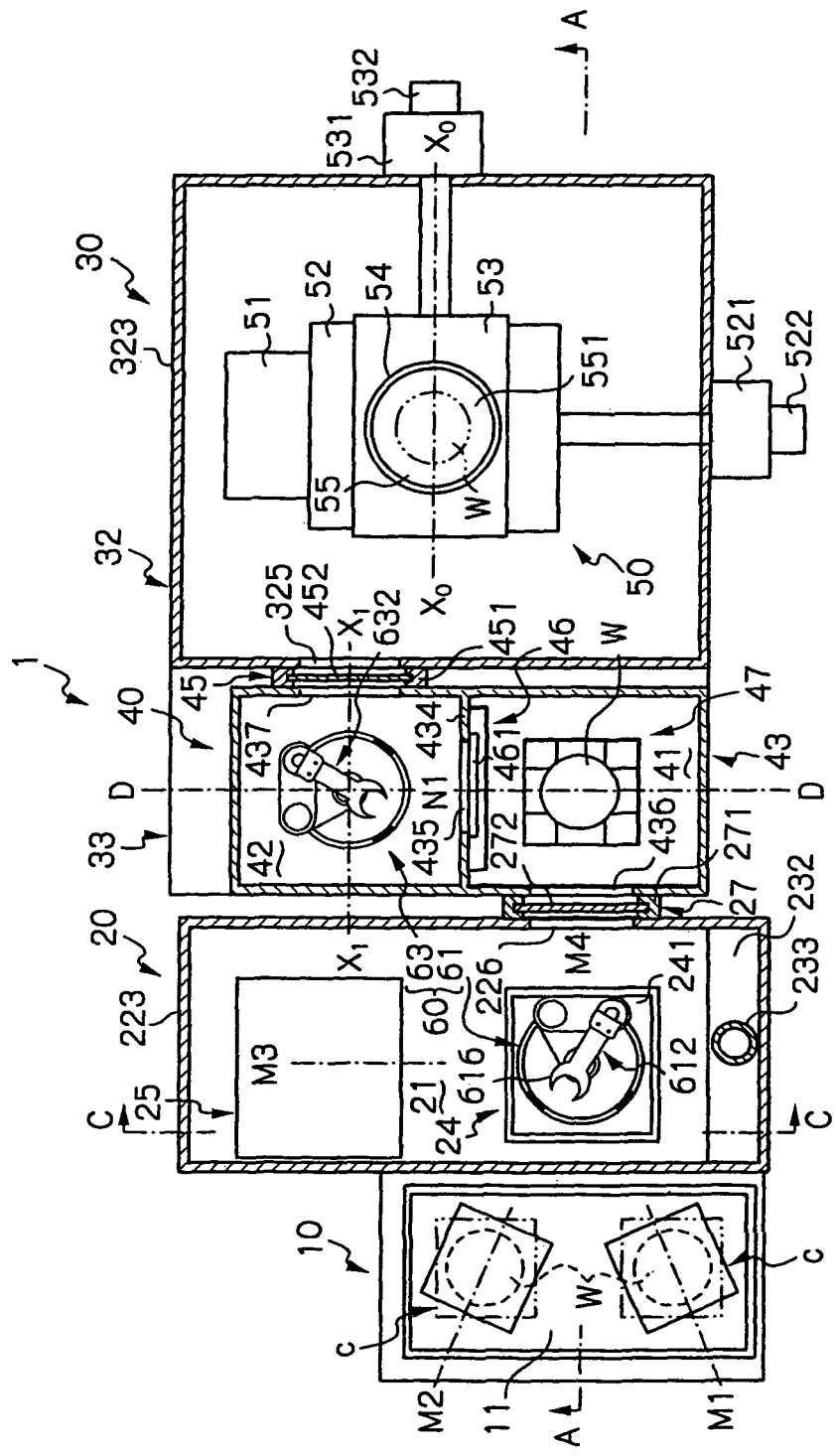
FIG. 2 is a top plan view of the main components of the inspection system illustrated in FIG. 1, taken along a line B-B in FIG. 1.

FIGS. 1 and 2 are an elevation and a plan view illustrating main components of the inspection system 1, respectively. The inspection system 1 comprises a cassette holder 10 for holding a cassette which contains a plurality of wafers; a mini-environment device 20; a main housing 30; a loader housing 40 disposed between the mini-environment device 20 and the main housing 30 for defining two loading chambers; a stage device 50 disposed within the main housing 30 for carrying a wafer W for movements; a loader 60 for loading a wafer from the cassette holder 10 onto the stage device 50 disposed within the main housing 30; and an electro-optical system 70 mounted in the main housing 30. These components are arranged in a positional relationship as illustrated in FIGS. 1 and 2. The inspection system 1 also comprises a pre-charge unit 81 disposed in the main housing 30 in vacuum; a potential applying mechanism for applying a potential to a wafer; an electron beam calibration mechanism; and an optical microscope 871 which forms part of an alignment control unit 87 (shown in FIG. 6) for aligning a wafer on the stage device 50. The inspection system 1 further comprises a control device 2 for controlling the operation of these components.

In the following, detailed description will be made of the configuration of the respective main components (sub-systems) of the inspection system 1.

Cassette Holder 10

The cassette holder 10 is configured to hold a plurality (two in this embodiment) of cassettes c (for example; closed cassettes such as SMIF, FOUP made by Assist Co.), each of which contains a plurality (for example, 25) of wafers arranged one above another in parallel. When a cassette is transferred and automatically loaded into the cassette holder 10 by a robot or the like, the cassette holder 10 having a suitable structure can be selected for installation. Alternatively, when a cassette is manually loaded into the cassette holder 10, the cassette holder 10 having an open cassette structure, suitable for the manual loading, can be selected for installation. In this embodiment, the cassette holder 10 is a type which allows the cassettes c to be automatically loaded, and comprises, for example, an up/down table 11, and an elevating mechanism 12 for moving up and down the up/down table 11. The cassette c can be automatically loaded onto the up/down table in a state indicated by a chain line in FIG. 2, and after the loading, is automatically rotated to a state indicated by a solid line in FIG. 2 to be oriented to the axis of rotation of a first transfer unit within the mini-environment device 20. The up/down table 11 in turn is moved down into a state indicated by a chain line in FIG. 1.

Figure 3:
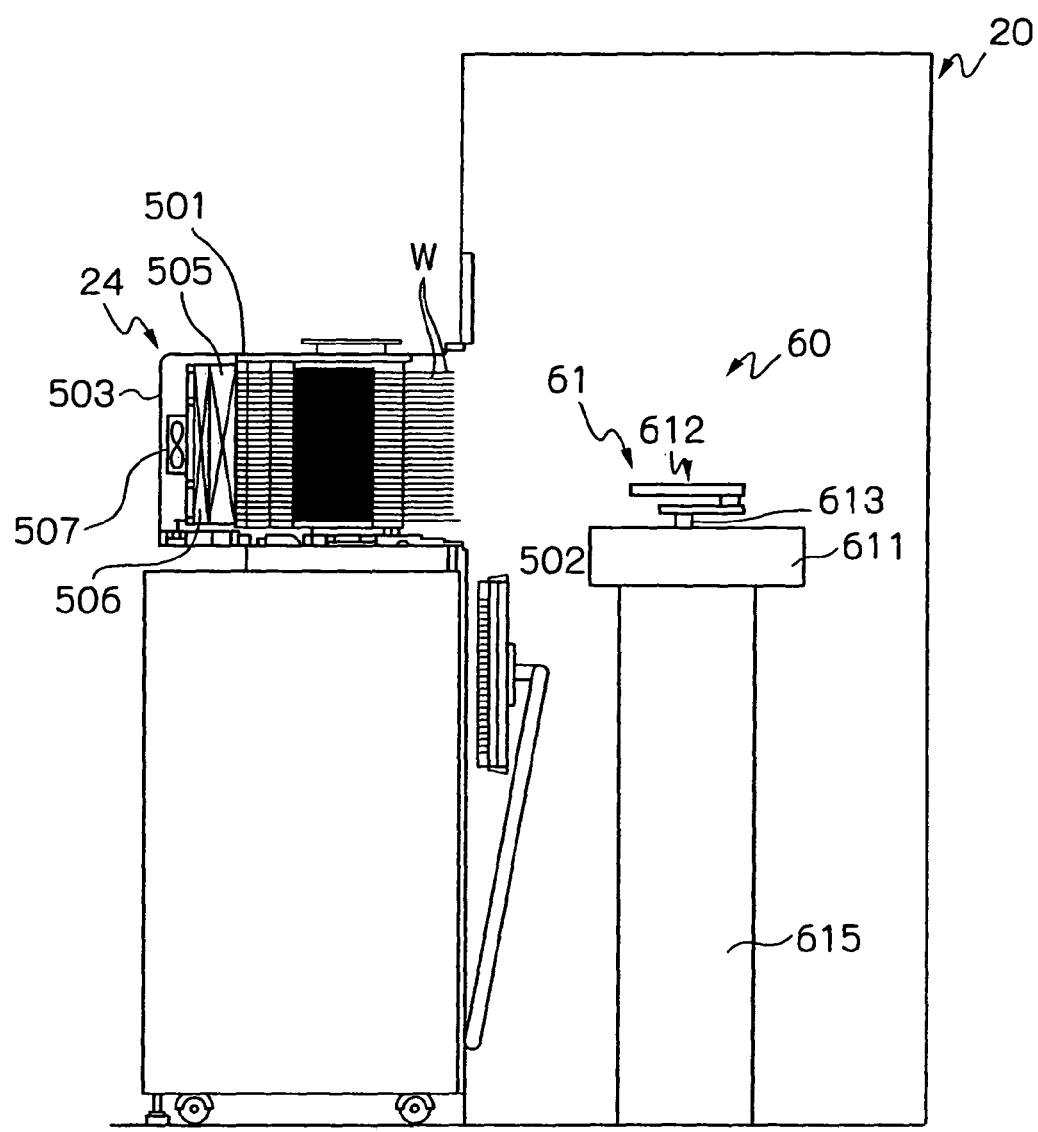
FIG. 3 is a diagram showing the relationship between a wafer carrier box and a loader in the inspection system illustrated in FIG. 1.

In another embodiment, as illustrated in FIG. 3, a plurality of 300 mm wafers W are placed in groove-shaped pockets (not shown) fixed inside a box body 501, transferred, and stored. A substrate carrier box 24 is coupled to the prism-shaped box body 501 and to an automatic gating device associated with a substrate transfer access door 502, and comprises the substrate transfer access door 502 for mechanically opening and closing an opening on a side surface of the box body 501; a lid 503 positioned opposite to the opening for covering the opening for mounting and removing filters and a fan motor; and a groove-shaped pocket 507 for holding wafers W. In this embodiment, wafers are transferred into and out of the box body 501 by a robot-type transfer unit 61 of the loader 60.

Wafers may be stored in the cassette c after the process for processing the wafers during the semiconductor manufacturing processes or during the process. Specifically, wafers which have undergone deposition, CMP, ion implantation and the like, wafers formed with wiring patterns on the surface thereof, wafers which have not been formed with wiring patterns may be stored in the cassette c for inspecting. Wafers stored in the cassette c are arranged one above another with a spacing therebetween and in parallel with one another, such that a first transfer unit, to be described later, can be moved up and down for holding a wafer at an arbitrary location within the cassette c with an arm thereof.

Mini-Environment Device 20

Figure 4:
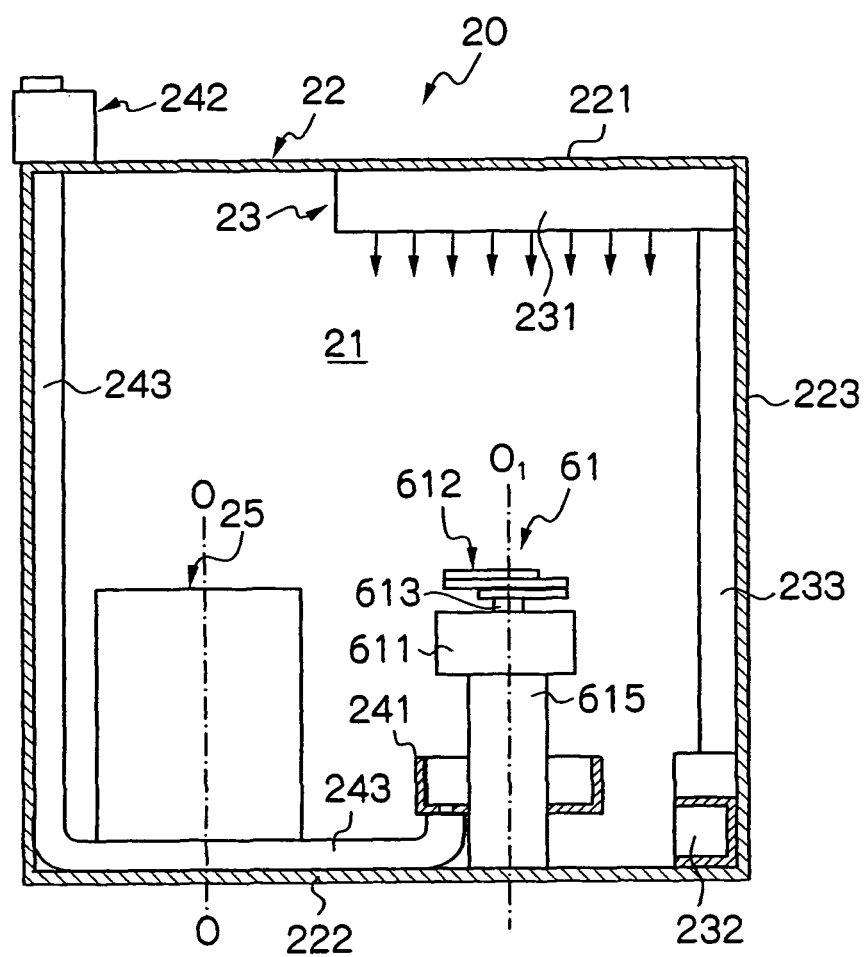
FIG. 4 is a cross-sectional view illustrating a mini-environment apparatus for use with the inspection system illustrated in FIG. 1, taken along a line C-C in FIG. 1.

FIG. 4 is an elevation of the mini-environment device 20, taken from a direction different from that in FIG. 1. As illustrated in FIG. 4 and the aforementioned FIGS. 1 and 2, the mini-environment device 20 comprises a housing 22 which defines a mini-environment space 21, the atmosphere of which is controlled; a gas circulator 23 for circulating a gas such as cleaning air within the mini-environment space 21 for controlling the atmosphere; a discharger 240 for recovering part of air supplied into the mini-environment space 21 for emission; and a pre-aligner 25 disposed within the mini-environment space 21 for roughly aligning a wafer which is a sample.

The housing 22 has a top wall 221, a bottom wall 222, and a peripheral wall 223 which surrounds the four sides of the housing 22, and is structured to block the mini-environment space 21 from the outside. For controlling the atmosphere within the mini-environment space 21, the gas circulator 23 comprises a gas supply unit 231 mounted on the top wall 221 to face downward for cleaning a gas (air in this embodiment) and supplying the cleaned air directly therebelow in laminar flow through one or more air blow ports (not shown); a recovery duct 232 mounted on the bottom wall 222 for recovering air which has flown down to the bottom from the gas supply unit 231; and a conduit 233 for connecting the recovery duct 232 to the air supply unit 231 for returning recovered air to the gas supply unit 231, as illustrated in FIG. 4.

The cleaned air, which goes down in laminar flow, is supplied such that it mainly flows through a carrying surface of a first transfer unit, to be described later, disposed within the mini-environment space 21, thereby preventing dust, possibly produced by the transfer unit, from sticking to wafers. A portion of the peripheral wall 223 of the housing 22 adjacent to the cassette holder 10 is formed with an access port 225.

The discharger 240 comprises a suction duct 241 disposed below a transfer unit, to be described later, at a position lower than the wafer carrying surface of the transfer unit; a blower 242 disposed outside the housing 22; and a conduit 243 for connecting the suction duct 241 to the blower 242. This discharger 240 aspires a gas flowing down around the transfer unit and including dust possibly produced by the transfer unit through the suction duct 241 for discharging the gas out of the housing 22 through the conduits 243, 244 and blower 242.

The pre-aligner 25 disposed within the mini-environment space 21 optically or mechanically detects an orientation flat (which refers to a flat portion formed near the outer periphery of a circular wafer) formed on a wafer, or one or more V-shaped notches formed on the outer periphery of a wafer, and preliminarily determines the position of the wafer in a rotating direction about the axial line $O_1$-$O_1$ of the wafer with an accuracy of approximately ±1 degree based on the detected orientation flat or V-shaped notches. The pre-aligner 25 forms part of a mechanism for determining the coordinates of the wafer, and is responsible for alignment of wafers.

Main Housing 30

As illustrated in FIGS. 1 and 2, the main housing 30, which defines a working chamber 31, comprises a housing body 32 which is supported by a housing supporting device 33 carried on a vibration blocking device, i.e., a vibration isolator 37 disposed on a base frame 36. The housing supporting device 22 comprises a frame structure 221 assembled into a rectangular shape. The housing body 32, which is securely placed on the frame structure 331, comprises a bottom wall 321 carried on the frame structure 331; a top wall 322; and a peripheral wall 323 connected to the bottom wall 321 and top wall 322 to surround the four sides of the housing body 32 to isolate the working chamber 31 from the outside. In this embodiment, the housing body 32 and housing supporting device 33 are assembled in rigid structure, and the vibration isolator 37 prevents vibrations from a floor on which the base frame 36 is installed from transmitting to the rigid structure. A portion of the peripheral wall 343 of the housing 32 adjacent to the loader housing 40 is formed with an access port 325 for carrying a wafer into and removing a wafer from the loader housing 40.

The working chamber 31 is held in vacuum atmosphere by a general purpose evacuator (not shown). Below the base frame 36, a control device 2 is disposed for controlling the operation of the entire inspection system 1.

In the inspection system 1, a variety of housings including the main housing 30 are evacuated, wherein an evacuation system used for it is composed of vacuum pumps, vacuum valves, vacuum gages, vacuum pipes, and the like for evacuating the electro-optical systems, detector, wafer chamber, load lock chamber and the like in accordance with a predetermined sequence. In the respective components, the vacuum valve is controlled to achieve a required degree of vacuum. Then, the degree of vacuum is monitored at all times, such that in the event of a failure, an urgent control is conducted by an interlock function to disconnect between chambers, or between chambers and emission system with isolation valves or the like, thereby ensuring a required degree of vacuum in each of the components. Vacuum pumps suitable for use with the inspection system 1 may be a turbo molecular pump for main emission, and a Roots-type dry pump for rough pumping. A site under inspection (electron beam irradiated site) may be at pressure in a range of $10^{-3}$ to $10^{-5}$ Pa, and preferably in a range of $10^{-4}$ to $10^{-6}$ Pa, lower by an order of magnitude, for a practical use.

Loader Housing 40

Figure 5:
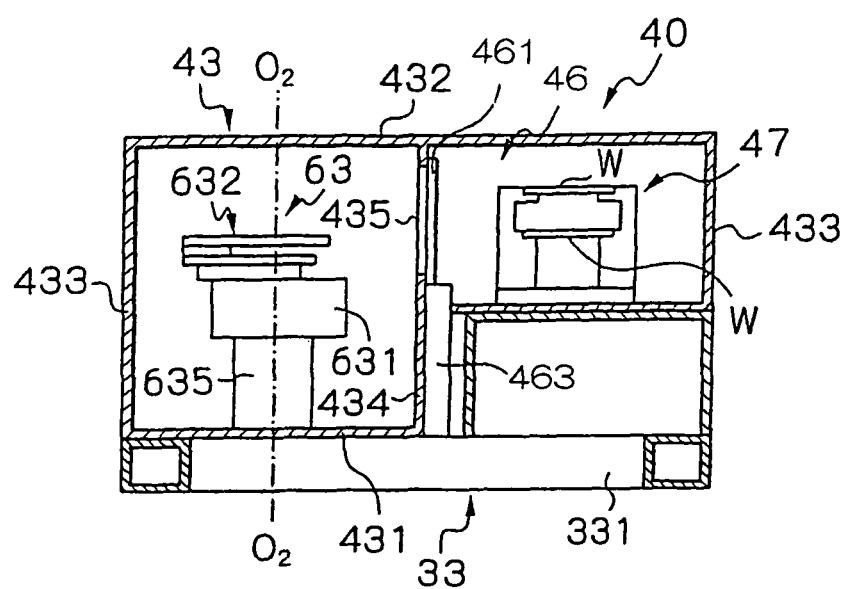
FIG. 5 is a diagram illustrating a loader housing for use with the inspection system illustrated in FIG. 1, taken along a line D-D in FIG. 2.

FIG. 5 illustrates an elevation of the loader housing 40 taken from a different direction from that in FIG. 1. As illustrated in FIGS. 5, 1, and 2, the loader housing 40 comprising a housing body 43 which defines a first loading chamber 41 and a second loading chamber 42. The housing body 43 comprises a bottom wall 431, a top wall 432, a peripheral wall 433 which surrounds the four sides of the housing body 43, and a partition wall 434 for partitioning the first loading chamber 41 from the second loading chamber 43, and isolates the two loading chambers from the outside. The partition wall 434 is formed with an opening, i.e., a port 435 for passing or receiving a wafer W between the two loading chambers. Also, a portion of the peripheral wall 433 adjacent to the mini-environment device 20 and main housing 30 is formed with gates 436, 437. The housing body 43 of the loader housing 40 is carried on and supported by the frame structure 331 of the housing supporting device 33. Therefore, no vibrations are transmitted to the loader housing 40 from the floor.

While the access port 436 of the loader housing 40 is in alignment to the access port 226 of the housing 22 of the mini-environment device 20, a shutter 27 is disposed between these access ports 436 and 226 for selectively blocking communications between the mini-environment space 21 and the loading chamber 41. Also, while the access port 437 of the loader housing 40 is in alignment to the access port 325 of the housing body 32 of the main housing 30, a shutter 45 is disposed between these access ports 436 and 325 for selectively blocking communications between the loading chamber 42 and the working chamber 31 in a sealing structure. Further, a shutter 46 is disposed in an opening formed through the partition wall 434 for closing the opening with a door 461 to selectively block communications between the first and second loading chambers in a sealing structure. These shutters 27, 45, 46 can hermetically seal the respective chambers when they are closed.

A wafer rack 47 is arranged within the first loading chamber 41 for horizontally supporting a plurality (two in this embodiment) of wafers W one above another with a space defined therebetween.

The first and second loading chambers 41, 42 are controlled to be in a high vacuum state by a general-purpose evacuator (not shown) including a vacuum pump (the degree of vacuum is in a range of $10^{-5}$ to $10^{-6}$ Pa). In this event, the first loading chamber 41 is held in a low vacuum atmosphere to serve as a low vacuum chamber, while the second loading chamber 42 is held in a high vacuum atmosphere to serve as a high vacuum chamber, thereby making it possible to effectively prevent wafers from contamination. With the employment of such a loading housing structure which comprises two loading chambers, wafers W can be transferred from the loading chamber into the working chamber without delay. Also, the employment of such a loading chamber structure can improve the throughput of a test for defects and the like, and approach the degree of vacuum around the electron source, which must be held in a high vacuum state, to a highest possible vacuum state.

Each of the first and second loading chambers 41, 42 is connected to an evacuation pipe and a vent pipe (not shown) for an inert gas (for example, dry pure nitrogen). With this structure, inert gas vent (an inert gas is injected to prevent an oxygen gas and the like other than the inert gas from sticking to the surface) is achieved in an atmospheric condition within each loading chamber.

It should be noted that in the main housing 30 which uses electron beams, representative lanthanum hexaboride ($LaB_6$) or the like for use as an electron source, i.e., an electron gun of the electro-optical system 70 should essentially be brought into contact with oxygen or the like with the least possible frequency in order not to reduce the life time thereof. Since the electron source is brought into contact with oxygen with reduced possibilities by conducting the atmospheric control as mentioned above before the wafers W are loaded into the working chamber which contains the electro-optical system 70 of the main housing 30, the life time of the electron source is less likely to be reduced.

Stage Device 50

The stage device 50 comprises a fixed table 51 disposed on the bottom wall 321 of the main housing 30; a Y-table 52 for movements on the fixed table 51 in a Y-direction (in the direction perpendicular to the sheet surface in FIG. 1); an X-table 53 for movements on the Y-table 52 in an X-direction (a left-to-right direction in FIG. 1); a rotary table 54 rotatable on the X-table 53; and a holder 55 disposed on the rotary table 54. Wafers W are releasably held on a wafer carrying surface 551 of the holder 55. The holder 55 may be of a general-purpose structure for releasably chucking a wafer W mechanically or in an electro-statically chucking manner. The stage device 50 operates a plurality of tables 52-54 mentioned above using servo motors, encoders, and a variety of sensors (not shown) for highly accurately aligning a wafer W held by the holder 55 on the carrying surface 551 in the X-, Y-, and Z-directions (an up-to-down direction in FIG. 1), as well as in a rotating direction (θ direction) about an axis normal to the wafer supporting surface with respect to electron beams irradiated from the electro-optical system 70.

For aligning a wafer in the Z-direction, the position of the carrying surface 551 on the holder 55 may be made finely adjustable in the Z-direction, by way of example. In this event, a reference position on the carrying surface 551 may be sensed by a position measuring device using a micro-diameter laser (a later interferometric telemeter using the principle of interferometer) for control by a feedback circuit (not shown), and additionally or alternatively, the position of the notch or orientation flat on a wafer may be measured to sense a planar position and a rotating position of the wafer with respect to an electron beam, and the rotary table 54 is rotated by a stepping motor or the like which can be controlled to operate in small angular increments. The wafers W may be directly placed on the rotary table 54 without providing the holder 55. For maximally preventing dust from occurring within the working chamber 31, the servo motors 521, 531 and encoders 522, 532 for the stage device 50 are disposed outside the main housing 30.

By previously inputting a rotating position and a position on the X-Y coordinate of the wafer W with respect to the electron beam into a signal detection system or an image processing system, later described, signals can be scaled as well.

Loader 60

The loader 60 (FIG. 12) comprises a robot-based first transfer unit 61 disposed in the housing 22 of the mini-environment device 20, and a robot-based second transfer unit 63 disposed in the second loading chamber 42.

The first transfer unit 61 has a multi-node arm 612 for rotation about an axis $O_1$-$O_1$ relative to a driver 611. While an arbitrary structure may be applied to the multi-node arm, this embodiment employs the multi-node arm 612 which has three parts attached for rotation relative to each other. A part of the arm 612 of the first transfer unit 61, i.e., a first part closest to the driver 611 is attached to a shaft 613 which can be rotated by a driving mechanism (not shown) in a general-purpose structure arranged in the driver 611. The arm 612 is rotatable about the axis $O_1$-$O_1$ by the shaft 613, and is telescopical in a radial direction relative to the axis $O_1$-$O_1$ as a whole through relative rotations among the parts. At the leading end of the third part furthest away from the shaft 613 of the arm 612, a chuck 616 is attached for chucking a wafer, such as a mechanical chuck in a general-purpose structure, an electrostatic chuck or the like. The driver is vertically movable by an elevating mechanism in a general-purpose structure.

In this first transfer unit 61, the arm 612 extends toward one of two cassettes c held in the cassette holder 10 in a direction M1 or M2 (FIG. 2), and a wafer W stored in the cassette c is carried on the arm, or is chucked by the chuck (not shown) attached at the leading end of the arm for removal. Subsequently, the arm is retracted (to the state illustrated in FIG. 2), and the arm is rotated to a position at which the arm can extend toward the pre-aligner 25 in a direction M3, and is stopped at this position. Then, the arm again extends to the pre-aligner 25 to transfer the wafer held by the arm thereto. After receiving the wafer from the pre-aligner 25 in a manner reverse to the foregoing, the arm is further rotated and stopped at a position at which the arm can extend toward the first loading chamber 41 (in a direction M4), where the wafer is passed to a wafer receiver 47 within the first loading chamber 41. It should be noted that when a wafer is mechanically chucked, the wafer should be chucked in a peripheral zone (in a range approximately 5 mm from the periphery). This is because the wafer is formed with devices (circuit wires) over the entire surface except for the peripheral zone, so that if the wafer were chucked at a portion inside the peripheral zone, some devices would be broken or defects would be produced.

The second transfer unit 63 is basically the same as the first transfer unit 61 in structure, and differs only in that the second transfer unit 63 transfers a wafer W between the wafer lack 47 and the carrying surface of the stage device 50.

The first and second transfer units 61, 63 transfer wafers from the cassette c held in the cassette holder onto the stage device 50 disposed in the working chamber 31 and vice versa while holding the wafer substantially in a horizontal posture. Then, the arms of the transfer units 61, 63 are moved up and down only when a cassette is extracted from the cassette c and loaded into the same, when a wafer is placed on the wafer lack and is extracted from the same, and when a wafer is placed on the stage device 50 and removed from the same. Therefore, the transfer units 61, 63 can smoothly move even a large wafer which may have a diameter of, for example, 30 cm.

Now, description will be made in order of the transfer of a wafer from the cassette c supported by the cassette holder 10 to the stage device 50 disposed in the working chamber 31 in the inspection system 1 having the configuration described above.

The cassette holder 10 for use in the inspection system 1 may have an appropriate structure either when cassettes are manually set or when cassettes are automatically set, as mentioned above. In this embodiment, as the cassette c is set on the up/down table 11, the up/down table 11 is moved down by the elevating mechanism 12 to bring the cassette c into alignment to the access port 225. As the cassette c is in alignment to the access port 225, a cover (not shown) disposed on the cassette c is opened, whereas a cylindrical cover is arranged between the cassette c and the access port 225 of the mini-environment device 20 to block the cassette c and mini-environment space 21 from the outside. When the mini-environment device 20 is equipped with a shutter for opening/closing the access port 225, the shutter is operated to open the access port 225.

On the other hand, the arm 612 of the first transfer unit 61 remains oriented in either the direction M1 or M2 (in the direction M1 in this description), and extends to receive one of wafers stored in the cassette c with its leading end as the access port 225 is opened.

Once the arm 612 has received a wafer, the arm 612 is retracted, and the shutter (if any) is operated to close the access port 225. Then, the arm 612 is rotated about the axial line $O_1$-$O_1$ so that it can extend in the direction M3. Next, the arm 612 extends to transfer the wafer carried on the leading end thereof or chucked by a chuck onto the pre-aligner 25 which determines a direction in which the wafer is rotated (direction about the center axis perpendicular to the surface of the wafer) within a predetermined range. Upon completion of the positioning, the first transfer unit 61 retracts the arm 612 after the wafer is received from the pre-aligner 25 to the leading end of the arm 612, and takes a posture in which the arm 612 can be extended in the direction M4. Then, the door 272 of the shutter 27 is moved to open the access ports 226, 436, permitting the arm 612 to place the wafer on the upper shelf or lower shelf of the wafer rack 47 within the first loading chamber 41. It should be noted that before the shutter 27 opens the access ports to pass the wafer to the wafer rack 47, the opening 435 formed through the partition 434 is hermetically closed by the door 461 of the shutter 46.

In the wafer transfer process by the first transfer unit 61, clean air flows in a laminar state (as a down flow) from the gas supply unit 231 disposed in the housing body 22 of the mini-environment device 20, for preventing dust from sticking to the upper surface of the wafer during the transfer. Part of air around the transfer unit (in this embodiment, approximately 20% of the air supplied from the gas supply unit 231, which is mainly contaminated) is aspired from the suction duct 241 of the discharger 24 for emission out of the housing body 22. The remaining air is recovered through the recovery duct 232 arranged on the bottom of the housing body 22, and again returned to the gas supply unit 231.

As a wafer is placed on the wafer rack 47 within the first loading chamber 41 of the loader housing 40 by the first transfer unit 61, the shutter 27 is closed to hermetically close the loading chamber 41. Then, the loading chamber 41 is brought into a vacuum atmosphere by expelling the air within the loading chamber 41, filling an inert gas in the loading chamber 41, and then discharging the inert gas. The vacuum atmosphere in the loading chamber 41 may have a low degree of vacuum. As the degree of vacuum has reached a certain level in the loading chamber 41, the shutter 46 is operated to open the access port 434, which has been hermetically closed by the door 461, and the arm 632 of the second transfer unit 63 extends to receive one wafer from the wafer receiver 47 with the chuck 616 at the leading end thereof (placed on the leading end or chucked by a chuck attached to the leading end). As the wafer has been received, the arm 632 is retracted, and the shutter 46 is again operated to close the access port 435 with the door 461. It should be noted that before the shutter 36 opens the access port 435, the arm 632 has previously taken a posture in which it can extend toward the wafer rack 47 in a direction N1. Also, as described above, before the shutter 46 opens the access port 435, the shutter 45 closes the access ports 437, 325 with the door 452 to block communications between the second loading chamber 42 and the working chamber 31, and the second loading chamber 42 is evacuated.

As the shutter 46 closes the access port 435, the second loading chamber 42 is again evacuated to a degree of vacuum higher than that of the first loading chamber 41. In the meantime, the arm 612 of the second transfer unit 61 is rotated to a position from which the arm 612 can extend toward the stage device 50 within the working chamber 31. On the other hand, in the stage device 50 within the working chamber 31, the Y-table 52 is moved upward, as viewed in FIG. 13, to a position at which the center line $X_0$-$X_0$ of the X-table 53 substantially matches an X-axis line $X_1$-$X_1$ which passes the axis of rotation $O_2$-$O_2$ of the second transfer unit 63. Also, the X-table 53 has moved to a position close to the leftmost position, as viewed in FIG. 2, and is waiting at this position. When the degree of vacuum in the second loading chamber 42 is increased to a level substantially identical to that of the working chamber 31, the door 452 of the shutter 45 is moved to open the access ports 437, 325, and the arm 612 extends so that the leading end of the arm, which holds a wafer, approaches the stage device 50 within the working chamber 31. Then, the wafer W is placed on the carrying surface 551 of the stage device 50. Once the wafer W has been placed on the stage device 50, the arm 612 is retracted, and the shutter 45 closes the access ports 437, 325.

The foregoing description has been made of a sequence of operations until a wafer W in the cassette c is transferred to the working chamber 31 and placed on the carrying surface 551 of the stage device 50. For returning a wafer W which has undergone a test from the stage device 50 to the cassette c, operations reverse to the foregoing are performed. Also, since a plurality of wafers are placed on the wafer rack 47, the first transfer unit 62 can transfer a wafer between the cassette c and the wafer rack 47 while the second transfer unit 63 is transferring a wafer between the wafer rack 47 and the stage device 50. Consequently, operations associated with the test can be efficiently conducted.

Electro-Optical System 70

An electro-optical system 70, which forms part of an electron beam apparatus, is a system for producing an image of a sample, and is available for SEM apparatus or arbitrary projection electron beam apparatus, which directs electron beams onto a sample to produce an image of the sample using secondary electrons, reflected electrons, and/or back scattered electrons. The resolution can be improved by using such an electron beam apparatus. It should be noted that detected electrons are not at all limited as long as they bear information on the surface of a sample, for example, mirror electrons (also referred to as "reflected electrons" in a broader sense) which do not directly impinge on a sample but reflect near the sample by the action of a reverse electric field formed near the surface of the sample, or transmission electrons which are transmitted through a sample, or the like.

Particularly, when mirror electrons are used, a resulting advantage is that the influence of charge-up is extremely low because the electrons do not directly impinge on a sample.

When mirror electrons are utilized, a sample is applied with a negative potential lower than an acceleration voltage to form a reverse electric field near the sample. This negative potential should be set at a value by which almost electron beams are drawn back near the surface of the sample. Specifically, the negative potential may be set at a level lower than the acceleration voltage of an electron gun by 0.5 to 1.0 volt or more. For example, when the acceleration voltage is −4 kV, the sample is preferably applied with a voltage of −4.000 kV to −4.050 kV. More desirably, the negative voltage is preferably set in a range of −4.0005 kV to −4.020 kV, and more preferably in a range of −4.0005 kV to 4.010 kV.

The electro-optical system 70 is disposed within a barrel 71 fixed to a main housing 30, and comprises an electron gun for emitting an electron beam(s) toward a sample surface; a primary electro-optical system including a deflector for deflecting the electron beam such that the electron beam from the electron gun scans on the sample; a secondary electro-optical system for leading electrons having information on the surface of the sample; and a detector for detecting the electrons led by the second electro-optical system to output image data of the surface of the sample.

It is further preferable that the electron gun is adapted to emit an electron beam(s) on the sample such that the emitted spot on the sample contains a plurality of pixels, and that the detector is adapted to image thereon the sample surface image based on the electrons having the sample surface information.

An X ray(s) is usable instead of an electron beam(s)

Pre-Charge Unit 81

The pre-charge unit 81 is disposed in close proximity to the lens column 71 of the electro-optical system 70 within the working chamber 31, as shown in FIG. 1. Since the inspection system 1 of the present invention irradiates a wafer with electron beams for scanning to test a device pattern and the like formed on the surface of the wafer, the wafer can be charged on the surface depending on conditions such as the material of the wafer, energy of irradiated electron beams, and the like. Further, the wafer surface may include a region which is more charged and a region which is less charged. In addition, while information on secondary electrons or the like generated by irradiation of electron beams is used for analyzing the wafer surface, possible variations in the amount of charge on the wafer surface may cause the information on the secondary electrons to include variations as well, thereby failing to provide accurate images. To prevent such variations in charge, the pre-charge unit 81 is provided in this embodiment. The pre-charge unit 81 includes a charged particle irradiating unit 811 which irradiates charged particles to a wafer before primary electron beams are emitted for testing, thereby eliminating variations in charge. A charged condition of the wafer surface can be detected by previously forming an image of the wafer surface using the electro-optical system 70, and evaluating the image. Then, the irradiation of charged particles from the charged particle irradiating unit 811 is controlled based on the detected charging state. The pre-charge unit 81 may irradiate blurred primary electron beams.

Alignment Control Unit 87

The alignment control unit 87 aligns a wafer W to the electro-optical system 70 using the stage device 50. The alignment control unit 87 is configured to control a low magnification alignment (alignment with a lower magnification than the electro-optical system 70) which is a rough alignment of a wafer through a wide field observation using the optical microscope 871 (FIG. 1); a high magnification alignment for a wafer using the electro-optical system 70; focus adjustment; setting of an area under inspection; pattern alignment; and the like. It should be noted that a wafer is tested at a low magnification as mentioned above because for automatically inspecting patterns on a wafer, an alignment mark must be readily detected by electron beams when the wafer is aligned by observing the patterns on the wafer in a narrow field of view using electron beams.

The optical microscope 871 is installed within the main housing 30, but may be movably disposed within the main housing 30. A light source (not shown) for operating the optical microscope 871 is also disposed within the main housing 30. Further, the electro-optical system involved in observations at high magnification, shares components, or primary and secondary optical systems 72 and 74 of the electro-optical system 70.

Figure 6:
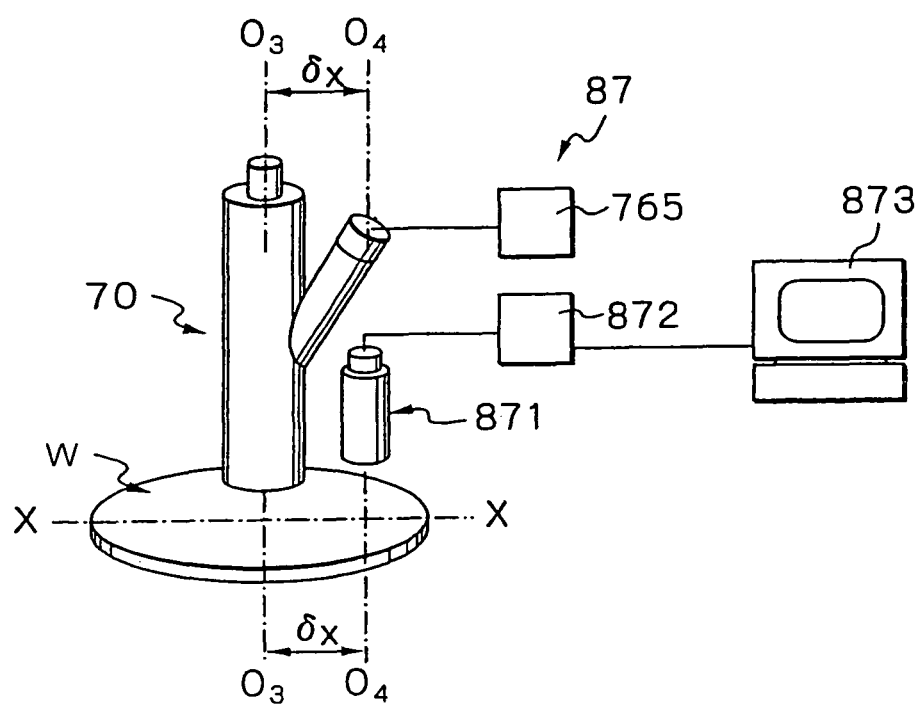
FIG. 6 is an explanatory diagram generally illustrating a wafer alignment controller which can be applied to an electro-optical system of the inspection system illustrated in FIG. 1.

FIG. 6 generally illustrates the configuration of the alignment control unit 87. For observing a site under observation on a wafer W at a low magnification, the site under observation on the wafer W is moved into the field of view of the optical microscope 871 by moving the X-stage or Y-stage of the stage device 50. The wafer W is viewed in a wide field of view using the optical microscope 871, and the site under observation on the wafer W is displayed on a monitor 873 through a CCD 872 to roughly determine where the site under observation is found. In this event, the magnification of the optical microscope 871 may be gradually changed from a low magnification to a high magnification.

Next, the stage device 50 is moved by a distance corresponding to a spacing δx between the optical axis of the electro-optical system 70 and the optical axis of the optical microscope 871, thereby moving the site under observation on the wafer W, which has been previously determined using the optical microscope 871, into the field of view of the electro-optical system 70. In this event, since the distance δx between the axial line $O_3$-$O_3$ of the electro-optical system 70 and the optical axis $O_4$-$O_4$ of the optical microscope 871 has been previously known (while both are shifted only in the X-direction in this embodiment, they may be shifted in the Y-direction), the site under observation can be moved to a viewing position of the electro-optical system 70 if the wafer W is moved by the distance δx. After the site under observation has been moved to the viewing position of the electro-optical system 70, the site under observation is imaged at a high magnification by the electro-optical system, and the resulting image is stored or displayed on a monitor 873.

After the site under observation of the wafer is displayed at a high magnification by the electro-optical system as described above, a displacement of the wafer in the rotating direction relative to the center of rotation of the rotary table 54 of the stage device 50, i.e., a shift δθ of the wafer in the rotating direction relative to the optical axis $O_3$-$O_3$ of the electro-optical system is detected by a known method, and a displacement of a predetermined pattern is detected in the X-axis and Y-axis directions relative to the electro-optical system 70. Then, the operation of the stage device 50 is controlled to align the wafer based on the detected values, data on a test mark separately attached on the wafer, or data related to the shapes of the patterns on the wafer.

Control Device 2

The control device 2 comprises a plurality of controllers such as main controller, IPE controller and stage controller.

A main controller is provided with a man-machine interface through which the operator performs operations (entering a variety of instructions/commands, recipes and the like, instructing the start of a test, entering all necessary commands for switching between an automatic and a manual test mode, commands involved in the manual test mode, and the like). Otherwise, the main controller is responsible for communications with the host computer in the factory, control of an evacuation system, transfer of wafers, control of positioning, transmission of commands to and reception of information from a stage controller and other controllers, and the like. The main controller also has a stage vibration correcting function for capturing an image signal from an optical microscope and feeding a stage fluctuation signal back to the electro-optical system to correct deteriorated images, and an automatic focus correcting function for detecting a displacement of a wafer observation position in the Z-axis direction (axial direction of the secondary optical system) and feeding the detected displacement to the electro-optical system to automatically correct the focus. The transmission and reception of feedback signals to and from the electro-optical system, as well as the transmission and reception of signals to and from the stage device are performed through the adjustment controller and stage controller, respectively.

The adjustment controller controls the electro-optical system 70, i.e., controls an electron gun, lenses, aligner, Wien filter and the like. In detail, the controller controls automatic voltage setting and the like for the respective lens systems and aligner corresponding to each operation mode (associative control); for example, controlling a power supply such that a constant electron current is irradiated to a target area at all times even if a different scaling factor is selected, and automatically setting voltages to the respective lens systems and aligner corresponding to each scaling factor.

The stage controller enables precise movements on the order of μm in the X-axis direction and Y-axis direction (with a tolerance of approximately ±0.5 μm), and also enables a control in the rotating direction (θ control) within an error accuracy of approximately ±0.3 seconds.

As described above, a wafer to be tested is transferred by the atmosphere transfer system and vacuum transfer system, aligned on the highly precise stage device (X-Y stage) 50, and then fixed by an electrostatic chucking mechanism or the like. Then, in a defect inspection process, an optical microscope is used to confirm the location of each die and detect the height of each location, as required, and such data is stored. The optical microscope is also used to capture an optical microscopic image of desired sites such as defects and to compare electron beam images. Next, conditions are set for the electro-optical system, and an electron beam image is used to modify the information set by the optical microscope to improve accuracy.

Next, information on recipes or specifications is entered to the apparatus depending on the type of wafer (after which process, whether the wafer size is 200 mm or 300 mm, and the like). Subsequently, after specifying a inspection place, setting the electro-optical system, setting inspection conditions, and the like, a defect test is normally conducted in real time while images are captured. A comparison of cells to one another, a comparison between dies, and the like are performed by a high speed information processing system which has associated algorithms installed therein, and the results are output to a CRT or the like, and stored in a memory, as required.

An embodiment of an electro-optical system 70 which forms an electron beam apparatus according to one embodiment of the present invention, will be described with reference to FIG. 7. The electro-optical system 70 is incorporated into the testing system illustrated in FIGS. 1 and 2 for use in testing samples such as wafers.

Figure 7:
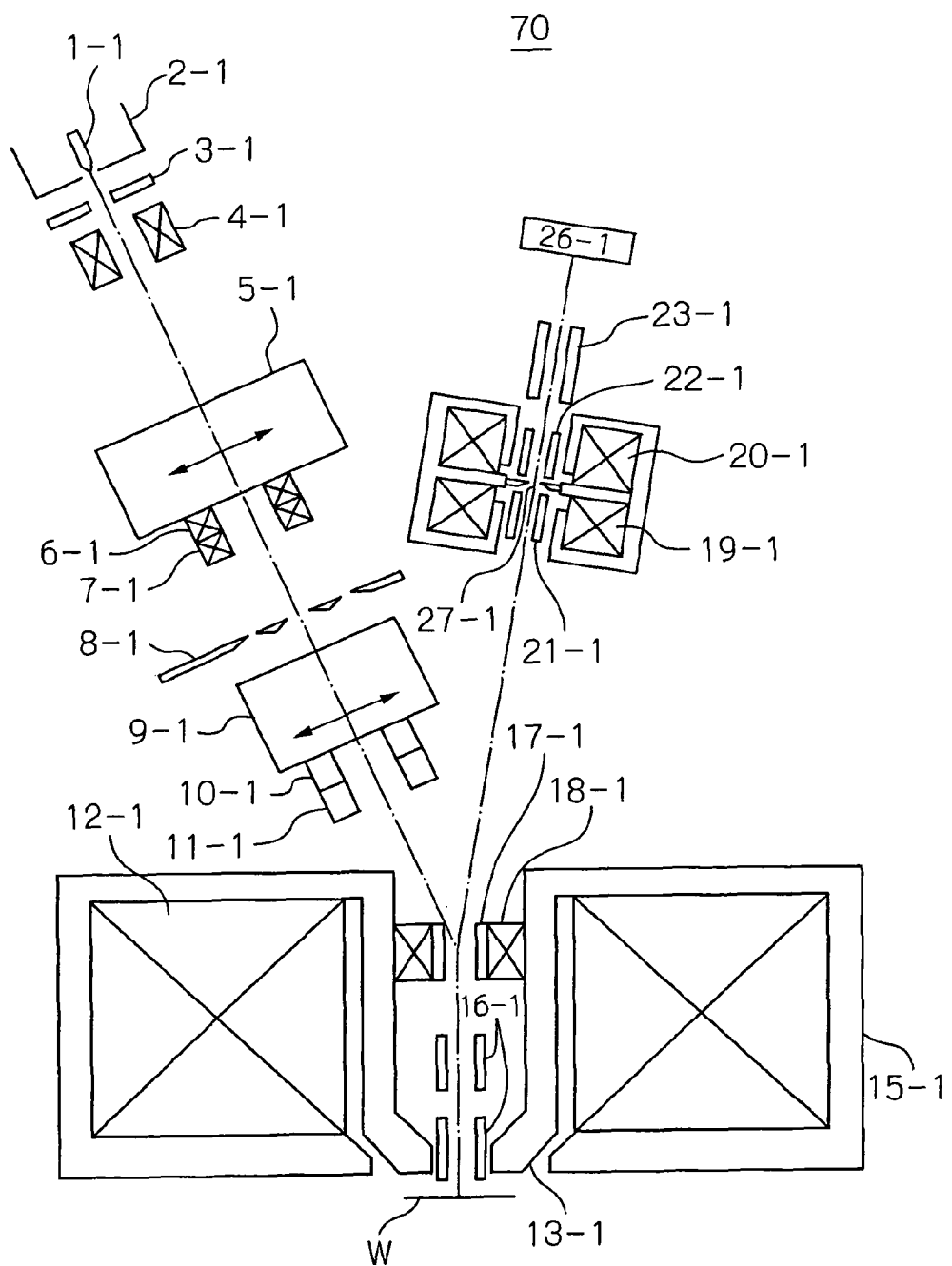
FIG. 7 is a schematic diagram showing a first embodiment of an electron beam apparatus according to the present invention.

The electro-optical system 70 illustrated in FIG. 7 is a projection type. In the electro-optical system 70, an electron beam emitted from an electron gun comprised of a $LaB_6$ cathode 1-1, a Wehnelt 2-1, and an anode 3-1 is converged by a condenser lens 5-1 to form a cross-over image in front of formation lens 9-1. An aperture plate 8-1 formed with an aperture for formation or shaping is placed in front of the position at which the cross-over image is formed, so that the electron beam is formed into a rectangular shape such as square by the aperture. The electron beam formed into a rectangular shape is reduced in size by the formation lens 9-1 and objective lens 12-1, and is then irradiated to a wafer W which is a sample. In this event, the cross-over image formed by the condenser lens 5-1 is converged by the formation lens 9-1 and focused on the main surface of the objective lens 12-1, thereby satisfying the Keller illumination condition.

Then, an adjustment is made by an alignment coil 4-1 so that the axis of the electron beam matches with the axis of the condenser lens 5-1, and another adjustment is made by alignment coils 6-1, 7-1 so that the axis of the electron beam matches with the aperture of the aperture plate 8-1 and the axis of the formation lens 9-1. Further, electrostatic deflectors 10-1, 11-1 deflect the rectangular electron beam so that the beam sequentially moves on the wafer W in a direction indicated by an arrow in FIG. 8, and so that the primary electron beam travels on a trajectory different from that of the secondary electron beam even below ExB separators 17-1, 18-1.

The objective lens 12-1 is a lens, which has a lens gap 13-1 beside the sample W, has small axial color aberration, and is configured to reduce the axial color aberration with a high voltage applied to an axially symmetric electrode 15-1. An axially symmetric electrode 16-1, which is disposed within the objective lens 15-1, is applied with a voltage which is adjusted to modify the position of an image formed by a secondary electron beam in front of magnifying lenses 19-1, 20-1, when a region of the wafer W spaced away from the optical axis is irradiated with an electron beam. Specifically, when the axially symmetric electrode 16-1 is applied with a positive voltage, the energy of the electron beam increases to reduce the lens action. As such, when the wafer W is irradiated with the electron beam in a region spaced away from the optical axis, an image can be formed substantially at the same focusing position as that obtained when the wafer W is irradiated with the electron beam in a region near the optical axis, by applying the axially symmetric electrode 16-1 with an adjusted voltage.

However, the image produced by the secondary electron beam differs, though slight, in the amount of rotation, when the electron beam is irradiated to a sub-visual field spaced away form the optical axis, as compared with that when the electron beam is irradiated to a region near the optical axis. Since the axially symmetric electrode 16-1 cannot correct the image for both the focus and amount of rotation, axially symmetric electrodes 21-1, 22-1 are disposed within the magnifying lenses 19-1, 20-1. By adjusting voltages applied to the electrodes, the image is corrected in such a manner that the posture of the image at the detector 26-1 matches with an arrangement of FOPs (fiber optical plates) which forms part of the detector, even when any sub-visual field is irradiated with the electron beam. The magnetic lenses 19-1, 20-1 are designed to generate magnetic fields which cause an image to rotate in the opposite directions. For example, when the axially symmetric electrode 21-1 is applied with a positive voltage while the axially symmetric electrode 22-1 is applied with a negative voltage, the amount of rotation caused by the magnetic lens 19-1 is reduced. In addition, the amount of rotation can be controlled by varying the applied voltages. In this way, the amount of rotation can be controlled by adjusting the polarities and values of the applied voltages, so that the rotating posture can be readily and rapidly adjusted, as compared with the amount of rotation which is controlled by adjusting a coil current.

Figure 8:
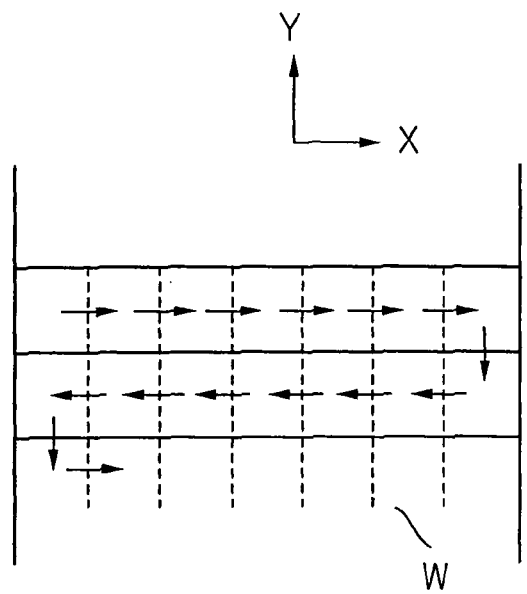
FIG. 8 is a diagram showing a scanning procedure executed by the electron beam apparatus illustrated in FIG. 7.
Figure 9:
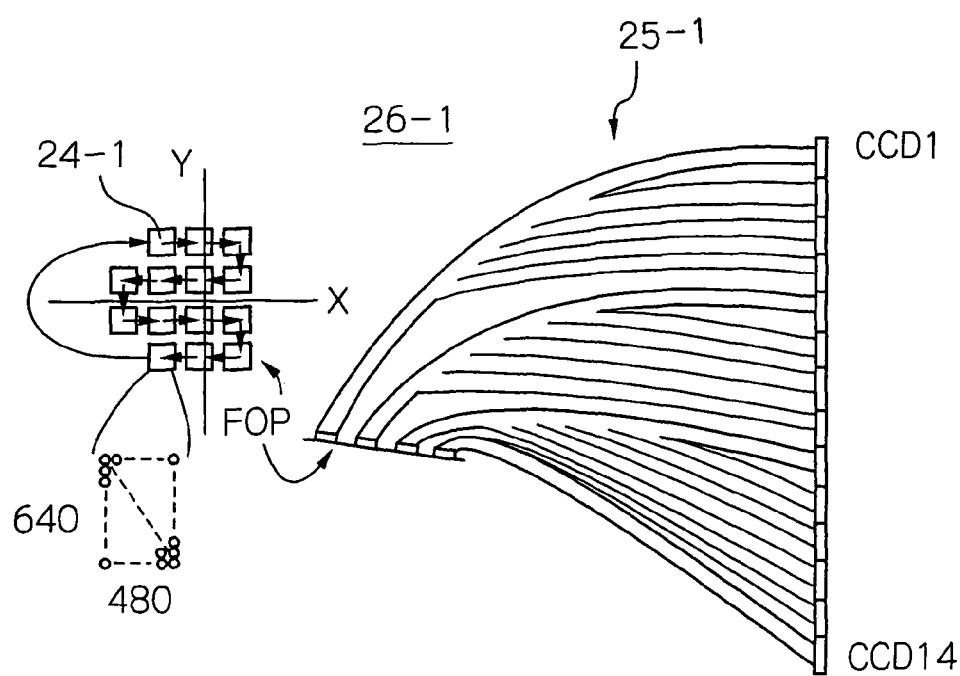
FIG. 9 shows a detection portion of the electron beam apparatus illustrated in FIG. 7.

As illustrated in FIG. 9, the detector 26-1 comprises fourteen FOPs 24-1 (~24-14) each coated with a scintillator, where a secondary electron beam is sequentially focused on the 14 FOPs in an order shown in FIG. 8, by deflecting the secondary electron beam by an electrostatic deflector 23-1 which operates to deflect it in synchronism with the scanning in the primary electro-optical system. Fourteen bundles of optical fibers 25-1 optically couple the 14 FOPs with 14 CCD detectors (CCD1~CCD14). Each bundle of optical fibers is composed of optical fibers aggregated in an array of 640 rows×480 columns, where each optical fiber corresponds to one pixel, and preferably has a diameter of 7.5 µmφ.

In this way, the detector 26-1 comprises a plurality of unit detectors arranged in matrix, where each unit detector comprises a combination of one FOP, a bundle of optical fibers (optical fibers arranged in m×n), and one CCD detector. It should be understood that the number of FOPs, as well as the number, diameter and the like of the optical fibers are not limited to the foregoing.

Now, a description will be given of the relationship between the number of unit detectors and an exposure time of FOP.

The FOP 24-$i$ ($i=1, 2, \ldots, 14$) has, for example, a minimum exposure time of 100 µs and a detection rate of 700 frames/sec. When the detection rate is 700 frames/sec, the resulting cycle time is 1.43 ms (=1/700).

Since the deflectors 10-1 and 11-1 for moving an electron beam from an illuminated region to another, as well as the deflector 23-1 for selecting one of 14 FOPs are all electrostatic deflectors, a settling time period of approximately 10 µs can be readily achieved, resulting in a total of the minimum exposure time period and the settling time period of the deflector equal to 110 µs (=100 µs+10 µs).

On the other hand, a time period required to fetch data from a CCD is 1.33 ms (=1.4 ms-100 µs).

In such a configuration, after the FOP 24-1 is exposed for 100 µs, data fetch from the CCD 1 connected to the FOP 24-1 through a bundle of optical fibers, is started. Then, after settling the driving of the deflectors and exposing the FOP 24-1 (i.e., after 110 µs from the end of the exposure of the preceding FOP), the FOPs 24-2, 24-3, ..., 24-14 are sequentially exposed. After exposure (100 µs) of each FOPi, the data fetch from the corresponding CCDi is started. In this event, a time period of 1.43 ms (=110 µs×13) is taken from a start of the data fetch from the CCD1 to a next start of the exposure for the FOP 24-1. Since the data has been completely fetched from the CCD1 within 1.43 ms (which is taken until the exposure of the FOP 24-1 is started again), the capture of a new image can be started after 1.43 ms.

As is apparent from the foregoing, data can be acquired at an optimal rate by setting the number of the unit detectors to a number larger tan $t_1/(t_2+t_3)$, where $t_1$ represents a time period required to fetch a signal from each CCDi; $t_2$ an exposure time period; and $t_3$ a settling time period of an electrostatic deflector.

The stage is moved in the Y-axis direction in FIG. 8, and an irradiated region on the wafer W is sequentially changed in the +X-axis direction and −X-axis direction alternately, while the stage is moved in the Y-axis direction. In this way, the irradiated region can be moved along arrows in FIG. 8. The beam is deflected in the Y-axis direction following motions of the stage, and after a sub-visual field is irradiated at one end of the frame, the beam is deflected by one visual field, in the direction opposite to the movement of the stage.

Also, each FOP 24-$i$ is made by fixing optical fibers of 7.5 µmϕ in an array of 640 rows×480 columns, polishing the surface of the array, and then coating the array with a scintillator. Since the optical fibers are fixed in the array at an incident end and an exiting end, an image will not be distorted while optical signals are being sent through the optical fibers. With an image of sample having one side of 50 nm, the sample must be enlarged by the electro-optical system. In this event, since the magnification is 150 (=7500 nm/50 nm), magnifying lens system can be configured with two stages (magnifying lenses 19, 20), where an objective lens may provide a 10× magnification and a magnifying lens a 15× magnification.

When pixels arrayed in 640×480 is exposed for 100 µs as mentioned above, a resulting pixel frequency is calculated to be 3.072 GHz (=640×480/(100×10$^{-6}$)). Thus, images can be captured at a high rate.

As described above, the electron beam apparatus of the first embodiment comprises a plurality of light receivers on the detection plane, each of which leads light to an independent CCD, and one CCD can be exposed while pattern data is fetched from another CCD. Accordingly, images can be captured on the order of GHz even if employed CCDs provide a small number of frames per second.

Also, the rotating posture of the electron beam can be corrected at high speeds by adjusting the voltages applied to the axially symmetric electrodes.

Figure 10:
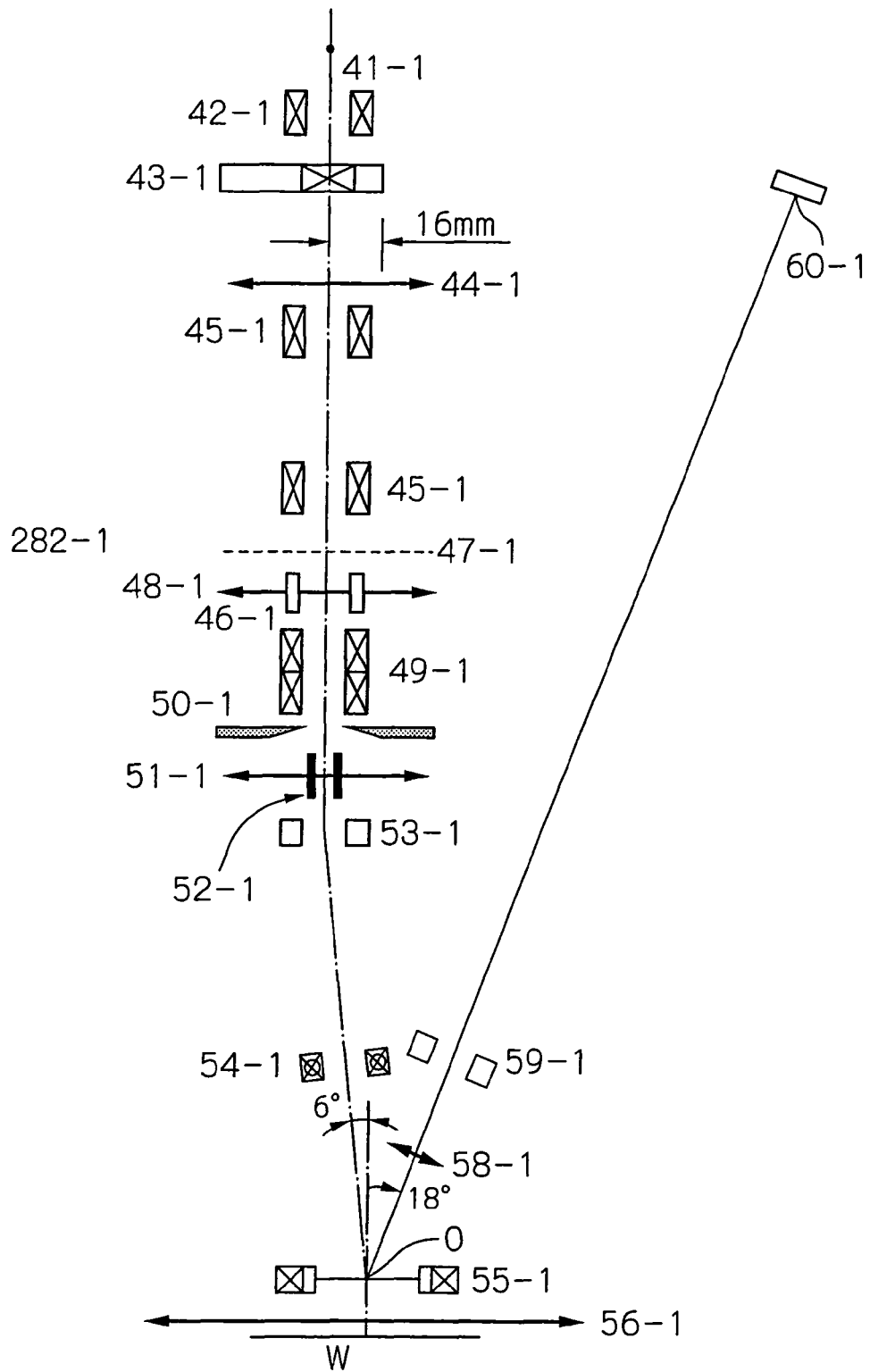
FIG. 10 is a schematic diagram showing a second embodiment of an electron beam apparatus according to the present invention.

FIG. 10 is an explanatory diagram illustrating an electro-optical system which forms an electron beam apparatus of a second embodiment according to the present invention. In the electron beam apparatus of this embodiment, an electron beam from a cross-over position 41-1 (formed by the electron beam emitted from an electron gun (not shown)) is converged by a condenser lens 44-1 to form a cross-over image in front of a multi-aperture plate 47-1 having multiple apertures. By irradiating the multi-aperture plate 47-1 with the electron beam diverted from the position at which the cross-over image is formed, multiple electron beams are formed and then a cross-over is formed on an NA aperture 50-1. Then, an enlarged image is formed on the main surface of an objective lens 56-1 through a reducing lens 51-1.

In this event, the electron beam which has passed the multiple apertures of the multi-aperture plate 47-1 transforms into multiple electron beams arrayed in 10 rows×10 columns, for instance, and they are reduced in size by the reducing lens 51-1 and the objective lens 56-1 for irradiation onto a sample wafer W. A condenser lens 48-1 in turn is a composite lens which can control the rotation of the beam by controlling currents of two coils. The reducing lens 51-1 is provided therein with an axially symmetric electrode 52-1 for dynamic focusing, which can dynamically correct the beams for changes in posture caused by the scanning of the multiple electron beams.

The axis (vertical direction) of the primary electro-optical system is parallel with the axis from an ExB separator 55-1 to the wafer W, but is offset in the horizontal direction, so that the electron beams are deflected toward the ExB separator 55-1 by an alignment deflector 53-1 for alignment. In one embodiment, the alignment deflector 53-1 and the ExB separator 55-1 are set in position such that the amount 16 mm of offset in the horizontal direction corresponds to 6°. In the ExB separator 55-1, the electron beams are deflected by 6° to the right on the drawing by an electrostatic deflector, and are again deflected by 12° to the left by an electromagnetic deflector. In this way, the electron beams travel in the vertical direction from the ExB separator 55-1. This separator 55-1 may be implemented by an electromagnetic deflector alone.

The wafer W is scanned by the deflector 53-1 and the electrostatic deflector of the ExB separator 55-1 to which a triangular wave multiplexed on a saw-tooth wave is applied. The triangular wave is used for the scanning in the X-axis direction, while the saw-tooth wave is used to continuously move the beams following motions of the stage in the Y-axis direction, and move the beams in steps at the ends of the visual field.

Secondary electrons which are emitted from irradiated points on the waver W by irradiating electron beams onto the wafer W, pass through the objective lens 56-1, and are deflected toward a secondary electro-optical system, for instance by 18° by the ExB separator 55-1. In the secondary electro-optical system, the beam intervals are increased by a magnifying lens 58-1 and the electron beams are detected at a detection unit unit 60-1 which comprises a plurality of detectors. In this event, an electrostatic deflector 59-1 is applied with a scanning signal in synchronism with the scanning of the electron beams in the primary electro-optical system, thereby permitting the secondary electron beams generated from the primary electron beams which are respectively associated with the second electron beams, to be always incident on the associated detectors, respectively.

Figure 11:
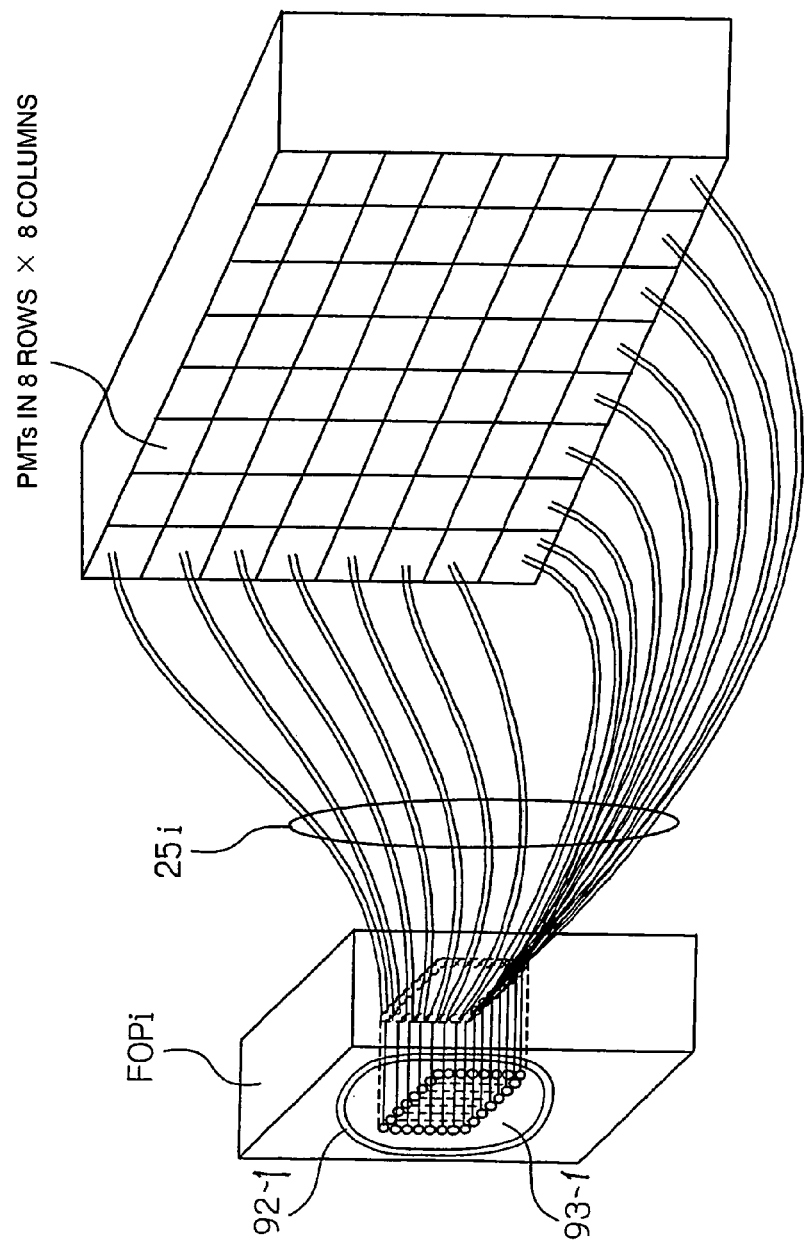
FIG. 11 shows a detection portion of the electron beam apparatus illustrated in FIG. 10.

FIG. 11 illustrates a configuration of the detection unit 60-1, which can be employed in the electron beam apparatus illustrated in FIG. 10. A vacuum window is formed of FOPi, which is formed on an array of fixed optical fibers 25$i$ each having a dimension of 4~16 µm. The array contains eight rows and eight columns. The detection unit 60-1 has a surface coated with a scintillator on a vacuum side, and is sealed by a contact face 92-1 of an O-ring. 64 optical fibers on the atmosphere side of the FOP are independent of one another, and are connected to corresponding ones of PMT light receiving planes which are arranged in eight rows×eight columns. Since each PMT light receiving plane has an area larger than the diameter of each optical fiber, the optical fiber may be simply brought into close proximity to the light receiving plane under a condition that light from the optical fiber does not introduce into adjacent light receiving planes. Alternatively, arbitrary opto-electric transducing elements such as photoelectric tubes may be used instead of using the PMTs.

Figure 12:
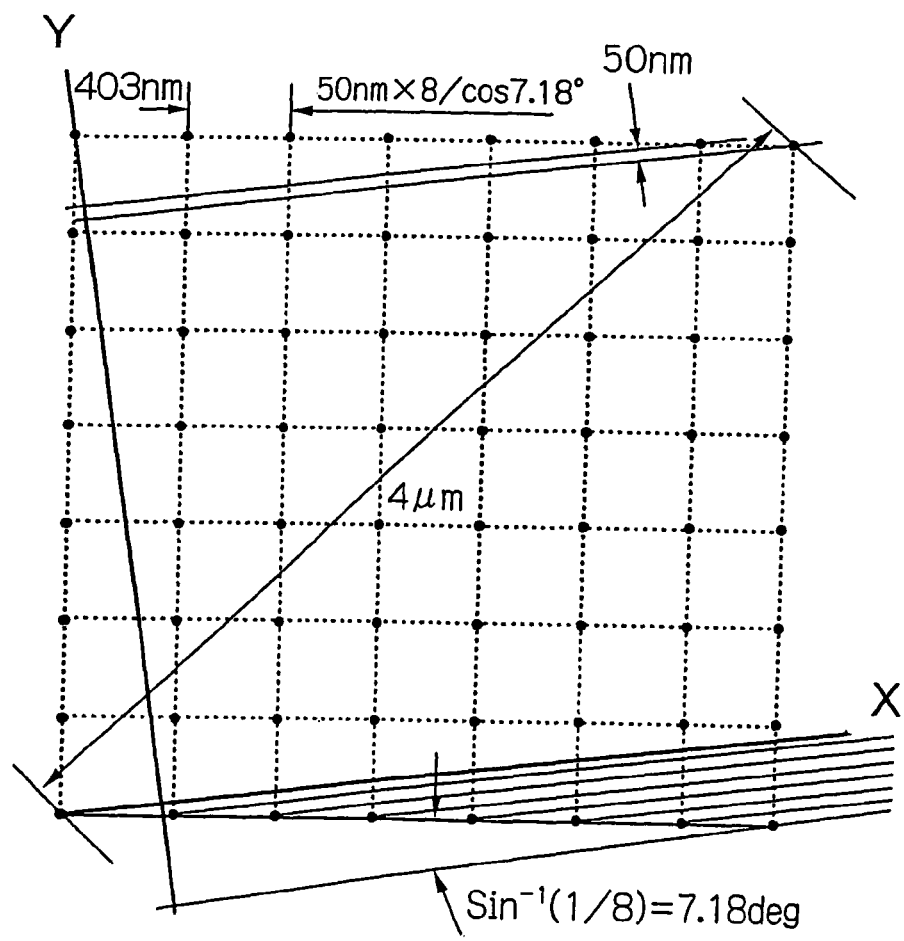
FIG. 12 is a diagram for explaining a multi-beam array and its scanning procedure in the electron beam apparatus illustrated in FIG. 10.

FIG. 12 represents the relationship between positions on a wafer irradiated with multiple electron beams, i.e., the optical axes. As shown in FIG. 12, 64 electron beams are arranged in a matrix of eight rows and eight columns in this embodiment, so that beam intervals of adjacent irradiated positions, i.e., the optical axes are 403 nm. Also, the matrix is rotated by sin$^{-1}$ (⅛) with respect to the X-Y orthogonal coordinates. By rotating the optical axes of the electron beams arranged in matrix with respect to the X-Y orthogonal coordinate system, when the electron beams are scanned in the X-direction, scanning lines in the matrix can be irradiated to a sample without interstice or at equal intervals without overlapping one another. Such 64 electron beams arranged for irradiation are scanned simultaneously in the X-axis direction by a predetermined scanning width, and then moved in steps by a distance 60 times as long as a raster width (50 nm in this example) in the Y-axis direction. Subsequently, the electron beams are scanned by the scanning width in the −X-axis direction, and again moved in steps in the Y-axis direction. Such scanning is repeatedly performed.

A reflection type projection microscope has been proposed for producing an image indicative of a potential image or potential distribution of a sample by irradiating a sheet or area beam to an area equivalent to a plurality of pixels, and totally reflecting the electrons (mirror electrons) without entering them into a sample. In such a reflection type projection microscope, when primary electron beams are reflected from positions spaced away from the surface of a sample, the resulting reflected beam does not contain information on the surface of the sample. Conversely, when the primary electron beams are reflected at positions excessively close to the surface of the sample, the electron beam is irregularly reflected due to asperities on the surface of the sample, resulting in a disturbed reflection image. Consequently, a problem arises in that potential information on patterns on the sample cannot be fetched in an effective manner.

To avoid the above problem, the present invention provides an apparatus which generates electron beams that are not totally reflected but are partially absorbed into a sample.

The aforementioned problem of the reflection type projection microscope will be described with reference to FIGS. 13(A)-(D). FIG. 13(A) illustrates a periodical line-and-space pattern, in which every other line patterns P1 have a potential of +1.1V, while the remaining line patterns P2 have a potential of −1.1V. In FIG. 13(A), V1 and V2 represent an equi-potential plane of +1.1V and an equi-potential plane of 0V, respectively.

A description will be given of a scenario where electron beams are irradiated to the patterns in the above state. In the following explanation, it is assumed that landing energy of electrons is 0 eV when the electron beams are incident on the patterns at potential of 0V, and the electron beams have an energy width of 2 eV provided by an $LaB_6$ electron gun.

As a converged electron beam E1 are irradiated to the pattern P1, incident electrons are substantially fully absorbed, because the pattern P1 is at potential of +1.1V, resulting in a small amount of reflected electrons. Stated another way, even electrons having energy smaller than the average by 1 eV still have energy of 0.1 eV when they reach the pattern P1, and are therefore absorbed into the pattern P1. For this reason, a small amount of secondary electrons are emitted and therefore a level of a produced signal is substantially zero.

On the other hand, when electrons E2 having energy smaller by +1 eV than the average, are irradiated to the pattern P2 at potential of −1.1V, the electrons E2 reduces the speed to zero at the time they reach the equi-potential plane V1 of +1.1V, and are accelerated in the opposite direction and therefore reflected. Electrons E3 having average energy reduces the speed to zero at the time they reach the equi-potential plane of 0V, and are reflected. Electrons E4 having energy larger by +1 eV than the average energy, are reflected before they reach the pattern P2, resulting in that a maximum amount of reflected electrons is obtained.

Therefore, a signal waveform as illustrated in FIG. 3(B) is produced when the pattern illustrated in FIG. 13(A) is scanned by electron beams.

Next, a description will be given of a scenario where a line-and-space pattern on a ragged substrate, instead of a substantially flat substrate, is scanned by electron beams, as illustrated in FIG. 13(C). Conditions other than the ragged substrate are similar to those in FIG. 13(A), so that electrons reflect depending on the energy thereof, as described in connection with FIG. 13(A).

That is, the electrons E2 having energy lower by 1eV than the average, reduces the speed to zero at the time they have passed slightly beyond the equi-potential plane V1 of +1.1V, and are reflected in the opposite direction. The electrons E3 having the average energy are reflected from the equi-potential plane V2 of 0V. The electrons E4 having energy larger by 1 eV than the average are reflected immediately before they are incident on the pattern P2.

When the substrate is ragged as illustrated in FIG. 13(C), electrons do not reflect in the vertical direction but reflect in accordance with incident angles to the equi-potential planes, due to irregular equi-potential planes V1, V2, resulting in electron scattering when electron beams are irradiated to peripheral regions of the patterns P1 and P2. For this reason, secondary electrons are more likely to fail to reach a detector, resulting in a lower signal strength. Accordingly, the waveform of a resulting signal is represented as illustrated in FIG. 13(D).

Also, when incident electrons have an energy width of 2 eV or more, part of electrons irradiated to the pattern P1 of +1.1V is not incident but reflected, so that a signal level corresponding to the zero level is offset. Further, part of electrons irradiated to the pattern P2 of −1.1V are also incident on this pattern, causing a reduction in the signal level corresponding to the one level. This results in a smaller amplitude of the signal.

Moreover, an amplitude of a signal is also reduced when a potential difference of patterns under evaluation is smaller than the potential difference of the example illustrated in FIG. 13(A).

In such an event, an FE electron gun, a TFE electron gun or a Schottky cathode electron gun may be used. This is because an energy width of electrons emitted by a TFE electron gun or the like is small, so that incident electrons are reflected or absorbed even in a small potential difference condition.

In a conventional electron beam apparatus which totally reflects incident electrons, the relationship between a cathode potential Vcc of an electron gun and a potential Vs on a sample is set to Vc>Vs. For example, Vc=−4 kV, and Vs=−4.01 kV.

On the other hand, in the electron beam apparatus of the present invention, Vc=Vs−(energy width)/2 is established. In this way, the present invention can substantially eliminate the landing energy of electrons having average energy on the surface of a wafer.

Also, when electron beams with an energy width of 2 eV are incident on a wafer, a signal waveform representative of a potential pattern on the wafer cannot be produced unless the potential patterns on the wafer have a potential difference of approximately 2V. However, when electron beams with an energy width of approximately 0.6 eV are incident on a wafer, a signal waveform representative of a potential pattern can be produced even when a potential difference is approximately 0.6V.

Then, in the second embodiment described above, since beams are emitted at intervals of 403 nm with respect to the pixel size of 50 nm, reflected beams can be efficiently detected even if the reflected beams slightly scatter as described in connection with FIGS. 13(C) and 13(D). Also, a potential contrast image can be produced at a high throughput.

Figure 14:
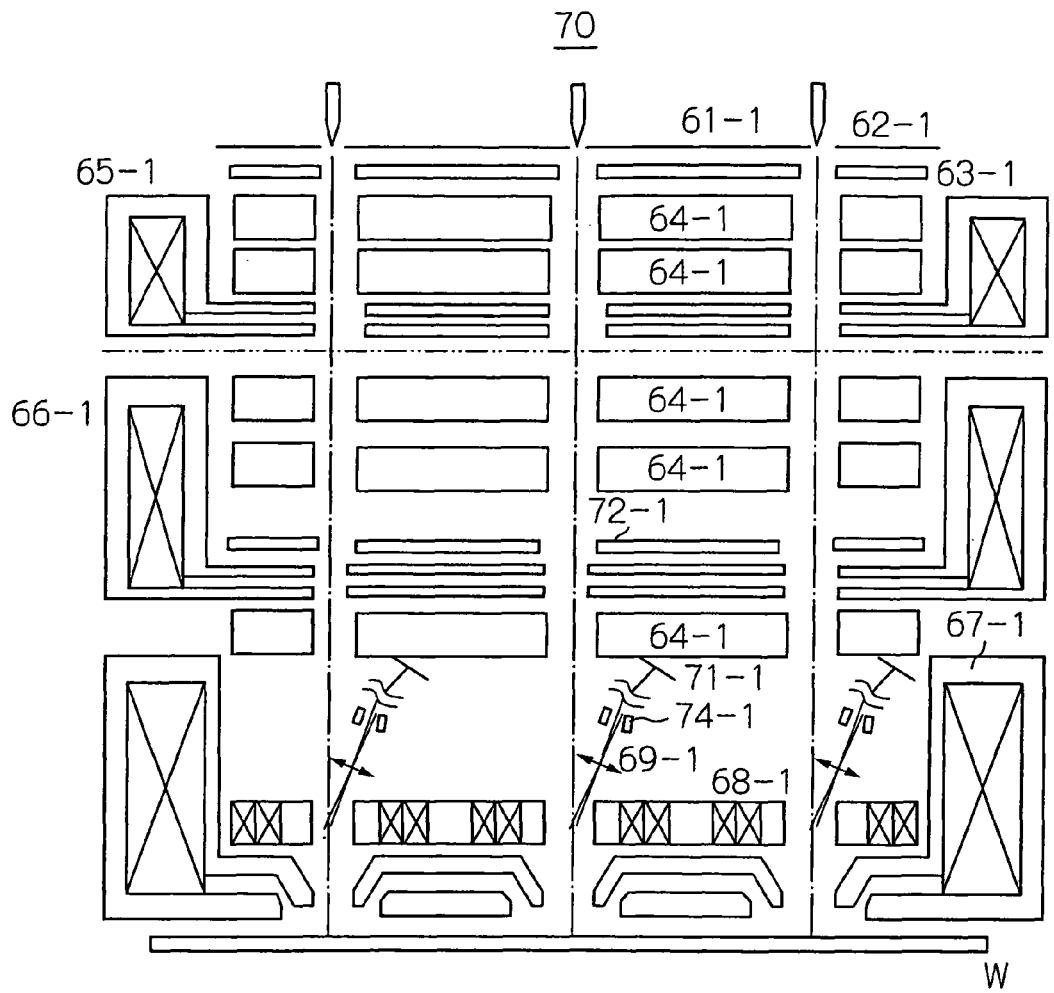
FIG. 14 is a schematic diagram showing a third embodiment of an electron beam apparatus according to the present invention.

FIG. 14 illustrates an electro-optical system in an electron beam apparatus of a third embodiment according to the present invention. An electron gun employed in this embodiment comprises a plurality of cathodes 61-1 arranged in a matrix of three rows and three columns, by way of example, to emit multiple electron beams. While the plurality of cathodes 61-1 are utilized, Wehnelts 62-1 and anodes 63-1 which form part of the electron gun are in an integrated structure for the cathodes, with one plate formed with a plurality of holes extending therethrough at positions coincident with a plurality of optical axes. A plurality of alignment deflectors 64-1 are provided, in each of which one ceramic substrate is formed with holes at positions corresponding to optical axes and with grooves for isolating eight electrodes (deflection electrodes). The substrate is non-electrolytically plated or metallically plated with NiP, except for portions required for isolation, thereby forming the electrodes while maintaining the isolation.

Each of a condenser lens 65-1, a reducing lens 66-1, and an objective lens 67-1 comprises two plates formed with holes at positions corresponding to optical axes, and a peripheral cylindrical structure for implementing a rib structure, and is provided with a lens exciting coil within the cylindrical structure. The peripheral rib structure can reduce distortions to a negligible level. The objective lens 67-1 has a lens gap on the side closer to a sample, i.e., a wafer W, thereby making it possible to reduce axial color aberration.

An ExB separator 68-1 is provided which may be composed of a combination of an X-deflection coil and a Y-deflection coil. It may employ a permanent magnet for one of the X- and Y-axis directions.

A multi-aperture plate 63-1 and an NA aperture plate 72-1 are provided each of which is formed by piercing multiple apertures through a single metal plate. In addition, they are also formed in a rib structure for preventing distortions.

An axially symmetric electrode may be provided within the objective lens 67-1 to correct field curvature aberration caused by the scanning of multiple electron beams. In addition, an axially symmetric electrode may be provided within the reducing lens 66-1 to correct rotation distortion caused by the scanning. By adjusting voltages applied to these axially symmetric electrodes, the respective rotations can be modified as mentioned above.

Secondary electrons emitted from the wafer W by the electron beams irradiated thereto pass through the objective lens 67-1, and are then deflected to the right in FIG. 14 by ExB separators 68-1 to enter the secondary electro-optical systems. Magnifying lenses 69-1 are disposed behind the respective ExB separators 68-1 to increase the intervals between secondary electron beams, which are then detected by detectors 71-1.

The scanning on the wafer W is performed by both the alignment deflector 64-1 and an electrostatic deflector of the ExB separator 68-1. In synchronism with the scanning of the primary electron beams, the secondary electron beams are deflected by the electrostatic deflector 74-1.

The detector 71-1 employed herein may be a detector configured as illustrated in FIG. 11.

Figure 15:
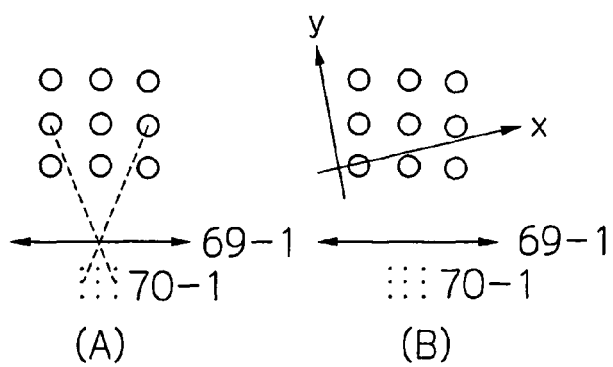
FIGS. 15(A) and (B) are diagrams for explaining relationships between a multi-beam arrangement on a sample and secondary electron beam images which have been magnified through a secondary electro-optical system in the electron beam apparatus illustrated in FIG. 14.

FIG. 15(A) represents a relationship between beams arranged on the wafer (reference numeral 70-1) and secondary electron images (circles) enlarged by the second electro-optical system, using the electron beam apparatus illustrated in FIG. 14, together with the magnifying lens 69-1. As illustrated in FIG. 15, the electron beams along the optical axes are arranged in a matrix of three rows and three columns, are enlarged by magnifying optical systems to dimensions represented by the circles in the drawing, respectively, and are detected by the detectors 71-1 without mutual interference. FIG. 15(B) in turn represents a relationship between the coordinates (X-Y orthogonal coordinates) of the X-Y stage which is the basis of the electron beam apparatus, and the enlarged secondary electron images (therefore, the beam array).

The relationship between the X-Y orthogonal coordinate system and the beam array will be described later in greater detail with reference to FIG. 17.

Figure 16:
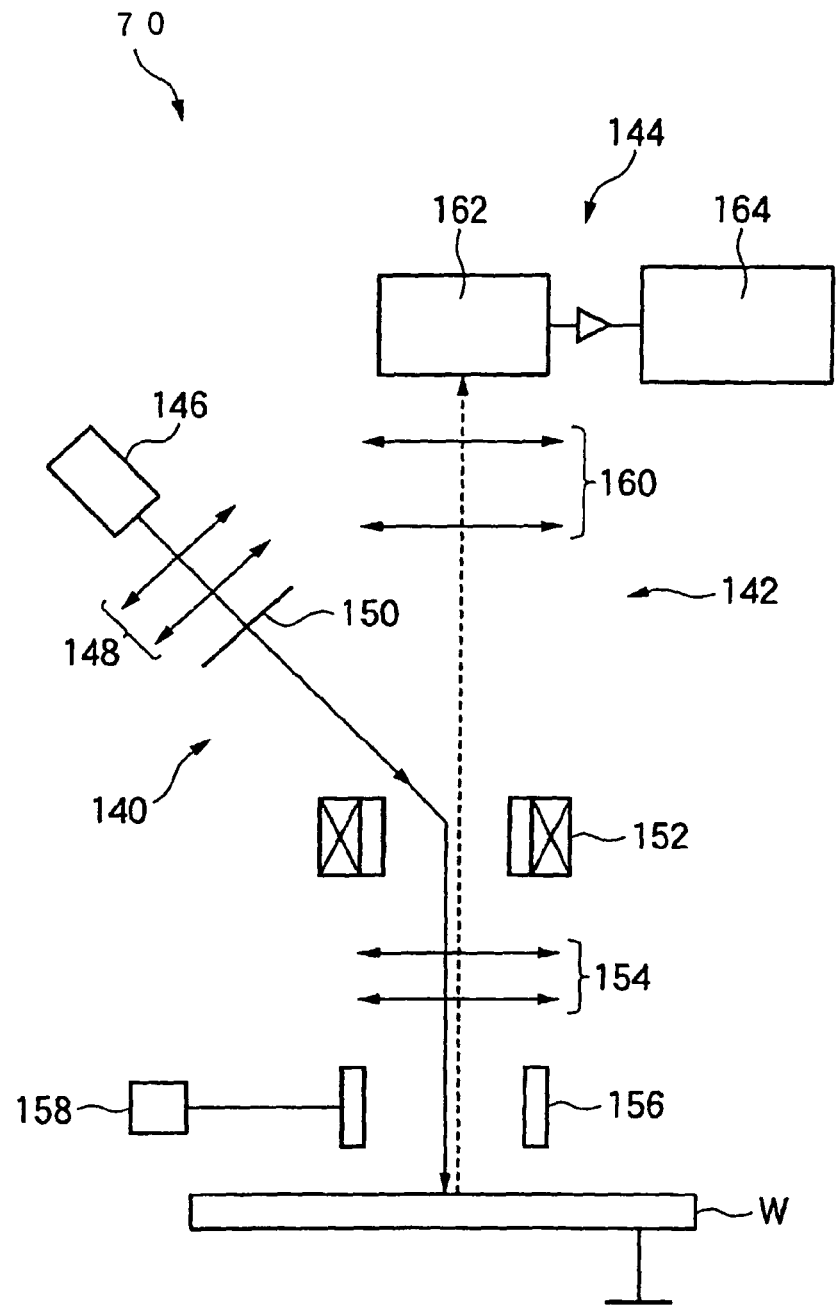
FIG. 16 is a schematic diagram showing a fourth embodiment of an electron beam apparatus according to the present invention.

FIG. 16 illustrates an electro-optical system 70 which forms part of the electron beam apparatus according to the third embodiment of the present invention. The electro-optical system 70 illustrated in FIG. 16 comprises an electron gun 146, a primary electro-optical system 140, a secondary optical system 142, and a detection unit 144. The primary electro-optical system 140 is an electro-optical system for irradiating electron beams formed electrons emitted from the electron gun 146 to a surface of a wafer W under testing, and comprises a lens system 148 including an electrostatic lens for converging primary electrons emitted from the electron gun 146; a multi-aperture plate 150 for forming a plurality of optical-axes, i.e., multiple beams; a Wien filter, i.e., ExB separator 152; and an objective lens 154. They are arranged in order with the electron gun 146 placed at the top, as illustrated in FIG. 16.

The objective lens 154 of this embodiment is a deceleration field type objective lens. In this embodiment, the optical axes of respective multiple beams, which are the primary electron beams formed through the multiple apertures 150 from the electrons emitted by the electron gun 146, are oblique to the axes (perpendicular to the surface of the wafer W) of the beams irradiated to the wafer W under testing. An electrode 156 is interposed between the objective lens 154 and the wafer W under testing. The electrode 156 has a shape axially symmetric to the axis along which the primary electron beams are irradiated, and is supplied a controllable voltage from a power supply 158.

The secondary electro-optical system 142 comprises a lens system 160 which includes an electrostatic lens that passes therethrough secondary electron beams separated from the primary electro-optical system 140 by the ExB deflector 152. This lens system 160 functions as a magnifying lens for magnifying secondary electron images.

The detection unit 144 comprises a detector 162 disposed on a focal plane of the lens system 160, and an image processor 164. The primary electron beams are generally incident in an E-direction (opposite to the electric field) of the ExB separator, and this direction is the same as an integration direction of an integration line sensor (TD1: time delay integration).

Now, it will be explained how the rotation of the stage is set when the pitch of optical axes is different from the die pitch, in the multi-beam electron beam apparatus according to the present invention (including a scenario where multiple beams are produced through multiple apertures, and a scenario where multiple beams are produced by a plurality of electro-optical barrels arranged in parallel).

Figure 17:
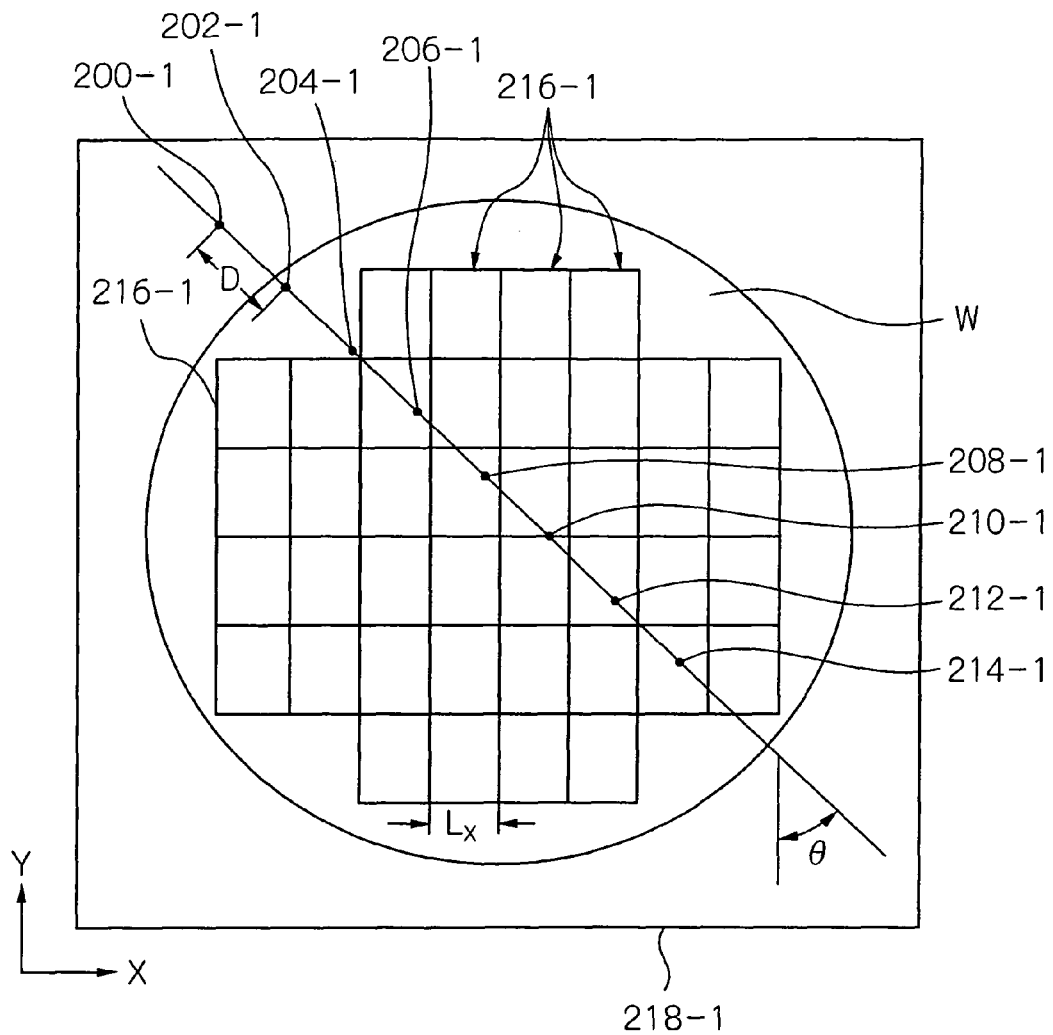
FIG. 17 is a diagram for explaining a relationship between a die pitch and a pitch of a plurality of optical axes in the X-direction.

FIG. 17 illustrates a plurality of optical axes 200-1, 202-1, 204-1, 208-1, 210-1, 212-1 and 214-1 on a wafer W which are arranged at an angle of about 45° to the Y-axis direction in which dies 216-1 are arranged. When the optical axes 200-1-214-1 are projected onto the X-axis, they are preferably arranged at intervals or pitches in the X-axis direction which are integer multiples of a pitch of the dies 216-1 in the X-axis direction, but the interval of the optical axes is not always an integer multiple of the die pitch. This is because such a die pitch often differs from one device product to another. In the example illustrated in FIG. 17, the arrangement pitch of the optical axes 200-1-214 in the X-axis direction is slightly smaller than the arrangement pitch of the dies in the X-axis direction. The difference between these pitches can be represented by $Lx - D^* \sin \theta$, where $Lx$ is the arrangement pitch of the dies 216-1 in the X-axis direction; $D$ is the arrangement pitch of the optical axes 200-1-216-1 in the X-axis direction; and $\theta$ is an angle between the Y-axis with the direction and a line along which the plurality of optical axes are arranged.

The wafer W is tested for defects and the like, while a sample stage 218-1 carrying the wafer W, is continuously moved in the Y-axis direction. When the leftmost optical axis 200-1, as viewed in FIG. 17, reaches a testing region of the first die (the topmost die on the first column from the left), the second optical axis 202-1 has not yet reached the second die (the topmost die on the second column from the left). This is because the pitch of the dies in the X-axis direction is larger than the pitch of the optical axes in the X-axis direction. Therefore, dies on the second column onward cannot yet be tested. Even if the second optical axis 202-1 enters the die testing region, the test cannot be always conducted immediately. Specifically, no test can be conducted unless the optical axis 202-1 matches with the center of the stripe. The present invention contemplates the following two methods for adjusting the optical axis to match with the center of the stripe.

A first adjusting method involves determining the value of the angle θ such that an integer m results from a division of the aforementioned pitch difference (Lx−D*sin θ) by the width of a standard stripe (i.e., one swath width). With the thus determined value of the angle θ, a test can be conducted using the optical axis 202-1 after pauses are made m times, in other words, after (a time required to scan one stripe) multiplied by m. Similarly, a test can be started with the optical axis 204-1 after pauses are made 2 m times; with the optical axis 206-1 after pauses are made 3 m times; with the optical axis 208-1 after pauses are made 4 times, with the optical axis 210-1 after pauses are made 5 m times; and with the optical axis 212-1 after pauses are made 6 m times. After dies on one column have been tested with the optical axis 200-1, the optical axis 200-1 is excluded from 7 m tests until the completion of tests of dies serviced by the optical axis 214-1.

For eliminating these pauses, θ may be determined such that the value of m is zero, i.e., such that the arrangement pitch Lx of the dies in the X-axis direction is equal to the arrangement pitch D*sin θ of the optical axes 200-1-214-1 in the X-axis direction. In this event, the angle must be largely deviated from 45°, and the sample stage 218-1 is set at the newly calculated angle θ, using a θ stage, and then, the dies are tested while the X-Y stage is continuously moved in the Y-axis direction in which the dies are arranged.

In this event, in the electron beam apparatus according to the present invention, the control unit 2 (FIG. 1) calculates θ which satisfies the following equation:

$(Lx-D*\sin\theta)/(\text{stripe width})=m$

In the equation, m is zero or a positive integer, using the pitch D of the optical axes in the electron beam apparatus, the die pitch Lx on the wafer W under testing in the X-axis direction, and the stripe width. Then, the rotating stage is controlled to rotate by the found angle θ. In this way, the first adjusting method mentioned above can be executed.

A second adjusting method involves varying the boundaries between the stripes from one die column to another, instead of fixing them at the same locations on all die columns. Assuming that the value of (Lx−D*sin θ)/(stripe width) is represented by integer m plus residue a, when a stripe having this dimension a of the residue is designated as the first stripe, the test can be conducted with minimized pauses. When the wafer W is rotated on the θ-stage to the new angle θ, the scanning direction of the EO system must also be rotated by a change in the angle θ.

In this event, in the electron beam apparatus according to the present invention, the control unit 2 calculates 0 which satisfies the following equation:

$(Lx-D*\sin\theta)/(\text{stripe width})=m+0$

In the equation, m is zero or a positive integer, using the pitch of the optical axes in the electron beam apparatus, the pitch D of dies on the wafer W under testing in the X-axis direction, and the stripe width. Then, the rotating stage (θ stage) is rotated by the calculated angle θ, and for a k-th column (k=2, 3, ... ), a narrower stripe having a width of a is designated as the first stripe, and a pause period is defined by m*k*(stripe manipulation time). Also, in accordance with this, the coordinate (X-axis coordinate) is converted for dividing the second and subsequent columns of the dies into stripes, and produced data is stored in correspondence to the converted coordinate.

In this way, the second adjusting method can be executed.

While the foregoing description has been made of an example in which a plurality of optical axes are arranged in one row, θ may also be determined in a similar manner in a case where the axes are arranged in a plurality of rows and a plurality of columns. For example, the relationship between the X-Y coordinates shown in FIG. 15(B) and positions irradiated with beams can be optimally set by the approach described above.

Figure 18:
FIG. 18 is a diagram illustrating a lens system having a plurality of axes, according to the present invention.

In the multi-beam electron beam apparatus illustrated in FIG. 16, the lenses such as the objective lens 154, condenser lens 148 and the like may be configured as shown in a cross-sectional view in FIG. 18.

In FIG. 18, three substrates 220-1, 222-1, 224-1 are accurately positioned, where holes 226-1, 228-1, 230-1 are aligned to match with the optical axis 214-1, by way of example. The substrates 220-1, 222-1 at both ends are applied with a reference potential, while the central substrate 224-1 is applied with a potential which satisfies lens conditions. A positive high voltage is applied for the objective lens 154, while a negative high potential is applied for the condenser lens 148 because aberration is not a concern. When the objective lens 154 is an electrostatic lens, a Schottky cathode electron gun may be utilized which exhibits low color dispersion because the electrostatic lens has large axial color aberration. Deflectors and ExB separator are also required, but a description thereon is omitted here, because their structures are described in detail in Japanese Patent Application No. 2002-316303 (JP-A-2004-152608). The lens configuration of FIG. 18 may be employed for the objective lens 67-1 of the electron beam apparatus in FIG. 14.

While the foregoing description has been given of a scenario where the pitch of the optical axes in the X-axis direction is not equal to the die pitch, generally, the interval of the optical axes multiplied by sin θ may be an integer multiple of the die pitch. That is, (n*Lx−D*sin θ)/(stripe width)=m may be satisfied (m: zero or positive integer, and n: positive integer). Further, since a larger value of m results in a longer pause period, the angle θ is preferably adjusted by the rotating stage to obtain m=3 or less.

Referring next to FIGS. 19(A) to 19(C), a test without adjusting the pitch of optical axes and the die pitch in the X-axis direction, will be explained. The distance or pitch between axes in the Y-axis direction may be determined irrespective of an arrangement of dies. Preferably, the distance Dx*sin θ between optical axes in the X-axis direction should be equal to or slightly smaller than a die size or die pitch Lx in the X-axis direction. Since the pitches are different to each other, one testing method may involve defining the first stripe of smaller dimensions such that the center of the second or subsequent stripe is placed on the optical axis, for stripes served by the second and subsequent optical axes. The boundary of the first stripe on the second column is determined in the following manner.

A description will be given with reference to FIG. 19(B). Reference numeral 232-1 designates a boundary of dies in the X-axis direction, and reference numeral 234-1 designates a boundary of the first stripe served by a beam of the second optical-axis. Reference numeral 236-1 designates an X-axis coordinate at the left end of a stripe before a test by the second optical axis. The spacing between reference numerals 234-1 and 238-1 is a standard stripe width. From the fact that the spacing between the boundaries indicated by reference numerals 236-1 and 232-1 is represented by (2Lx−Dx), assuming that a narrower stripe is present between the boundaries indicated by reference numerals 232-1 and 234-1, it is represented in the following equation:

2*(Standard Stripe Width)=(2Lx−Dx)+Narrower Stripe i.e., Narrower Stripe=2*(Standard Stripe Width)−(2Lx−Dx), In general, Narrower Stripe=m*Standard Stripe Width−(n*Lx−Dx)

where m is a minimum positive integer which satisfies (n*Lx−Dx)/Standard Stripe Width<m, and n is an integer that the pitch of optical axes is the closest to the die pitch multiplied by n. For the narrower stripe between the boundaries indicated by reference numerals 232-1 and 234-1, m=2, and n=2.

In this event, the control unit 2 (FIG. 1) also calculates m, n, and the width of the narrower strip which satisfy the foregoing equation. From the third column onward, the narrower stripe determined by the same method as above is first placed, and subsequently, the test is conducted with the standard stripe width. Then, in accordance with the placement of the narrower stripe, the coordinate (X-axis coordinate) is converted for dividing dies on the second and subsequent columns; and generated image data is stored in correspondence to the converted coordinate.

Referring now to FIG. 19(C), a description will be given of another method which is available when there is no integer-multiple relationship between the pitch of optical axes and the die pitch in the X-axis direction. Reference numeral 236-1 designates the X-axis coordinate at the left end of a stripe associated with the second optical axis, and reference numeral 232-1 designates a boundary of dies in the X-axis direction. When the distance 2Lx−Dx between reference numerals 236-1 and 232-1 is an integer multiple of the stripe width, all dies can be divided into stripes of the same width, and can be tested for defects. Specifically, the stripe width is only required to satisfy, and is smaller than the dimension of the visual field which can be scanned by an EO system:

(m*Lx)/(stripe width)=n

FIGS. 20(A) and 20(B) illustrate one embodiment of an objective lens when the optical axes are two-dimensionally arranged. FIG. 20(A) is a top plan view, and FIG. 20(B) is a cross-sectional view taken along a B-B line in FIG. 20(A). Four optical axes 240-1 are provided for the first column; six each for the second and third columns; and four for the fourth column, and they are positioned over a wafer. In the objective lens 242-1, each of inner magnetic poles 244-1 and outer magnetic poles 246-1 comprises a single disk made of a ferromagnetic material and formed with circles, and they are assembled such that the optical axes are in common. The objective lens 242-1 further comprises an excitation coil 248-1 and a magnetic circuit 250-1 around its periphery, and is formed with lens gaps 252-1 at a side closer to the wafer. As illustrated, the lens gap 252-1 forms part of two cones. In more detail, the bottom surface of the inner magnetic pole 244-1 forms a part of the outer surface of the cone, while the top surface of the outer magnetic pole 246-1 forms a part of the inner surface of the cone. The lens gap 252-1 is a gap defined by the outer surface and inner surface of the cone.

As another method of two-dimensionally arranging optical axes, such a method of two-dimensionally arranging barrels each having a small outer diameter as described in "Microscope of Thumb Size" (by Miyoshi, see Applied Physics, Vol. 73, No. 4, 2004) may be adopted.

Since the present invention is configured as described above, images can be captured on the order of GHz even using an area sensor which senses a small number of frames per second in an electron beam apparatus which comprises a projection type electro-optical system. Accordingly, by using the electron beam apparatus of the first to fourth embodiments according to the present invention for testing and evaluating a wafer for defects and the like during a semiconductor device manufacturing process, the test and evaluation can be conducted at high throughput and high accuracy, so that semiconductor devices themselves can be manufactured at high throughput and high accuracy.

Also, even the die pitch in the X-axis direction is different from the pitch of optical axes in the X-axis direction, problems possibly resulting therefrom can be reduced.

The invention claimed is:

1. An electron beam apparatus, comprising:
    an electron gun configured to emit a single primary electron beam;
    a first deflector configured to deflect the single primary electron beam to irradiate each of a plurality of sub-visual fields which are obtained by dividing an evaluation area on a surface of a sample;
    a detection device configured to detect secondary electrons containing information on the surface of the sample in each of the plurality of sub-visual fields to acquire information on the evaluation area, said detection device comprising a plurality of unit detectors, each of said plurality of unit detectors including an area sensor, a bundle of optical fibers having a first end coupled to a detection plane of said area sensor, and an FOP optically coupled to a second end of said bundle of optical fibers and formed with a scintillator, on which a secondary electron beam of the sub-visual fields is focused,
    a second deflector configured to deflect the secondary electron beam emitted from the sub-visual fields each time the single primary electron beam is irradiated to the next sub-visual field, so as to move the secondary electron beam sequentially over a surface of said FOP of each of said plurality of unit detectors which form said detecting device,
    an electromagnetic objective lens including a lens gap beside the sample and a first axially symmetric electrode therein, said electromagnetic objective lens being configured to form an image produced by the secondary electron beam of the sub-visual fields substantially at the same focusing position in a state in which the sub-visual fields spaced away from the optical axis and the sub-visual fields near the optical axis are irradiated by the single primary electron beam, by adjusting polarities and values of voltages applied to said first axially symmetric electrode, and
    two electromagnetic magnifying lenses, each of said two electromagnetic magnifying lenses including a second axially symmetric electrode therein and being configured to correct an amount of rotation of the image to match with an arrangement of said FOP of each of said plurality of unit detectors by adjusting polarities and values of voltages applied to said second axially symmetric electrode, a number of said plurality of unit detectors being set to a value approximated to $t_1/(t_2+t_3)$, where $t_1$ represents a time period required to fetch a signal from one area sensor, $t_2$ an exposure time period, and $t_3$ a settling time period of said second deflector, and said FOP of each of said plurality of unit detectors having optical fibers fixed in an array and polished and coated by said scintillator.

2. The electron beam apparatus according to claim 1, further comprising a primary electro-optical system including a plurality of optical axes which are formed by a plurality of lenses comprising magnetic poles or electrodes having lens gaps.

3. The electron beam apparatus according to claim 1, wherein said electron beam apparatus is configured to evaluate the sample including patterns which differ in potential, and information on the evaluation area is information on the potential.

4. The electron beam apparatus according to claim 1, wherein said detection device has a surface coated with said scintillator on a vacuum side.

5. The electron beam apparatus according to claim 1, wherein said detection device is sealed by a contact face of an o-ring.

6. The electron beam apparatus according to claim 1, wherein said first deflector is configured to deflect the single primary electron beam to sequentially irradiate each of the plurality of sub-visual fields, the sub-visual fields being arranged in a square on the evaluation area.

7. The electron beam apparatus according to claim 6, wherein said second deflector is configured to deflect the secondary electron beam sequentially over said surface of said FOP of each of said plurality of unit detectors so as to correspond to the sequential irradiation of each of the plurality of sub-visual fields by the single primary electron beam.

8. The electron beam apparatus according to claim 1, wherein said second deflector is electromagnetic.

9. The electron beam apparatus according to claim 1, wherein said second deflector is electrostatic.

10. The electron beam apparatus according to claim 1, wherein said electron beam apparatus is configured to enlarge the sample in a first stage and a second stage, the first stage providing a 10× magnification and the second stage providing a 15× magnification.

11. The electron beam apparatus according to claim 1, wherein said FOP of each of said plurality of unit detectors has a 640 row×480 column array of 7.5φ optical fibers.

* * * * *